United States Patent
Manterola Careaga et al.

(10) Patent No.: US 8,148,334 B2
(45) Date of Patent: Apr. 3, 2012

(54) PEPTIDES WITH CAPACITY FOR BINDING WITH INTERLEUKINE 10 (IL-10)

(75) Inventors: Lorea Manterola Careaga, Pamplona-Navarra (ES); Inés Noelia Casares Lagar, Pamplona-Navarra (ES); Nancy Díaz-Valdés Farray, Pamplona-Navarra (ES); Javier Dotor de las Herrerías, Pamplona-Navarra (ES); Juan José Lasarte Sagastibelza, Pamplona-Navarra (ES); Pablo Sarobe Ugarriza, Pamplona-Navarra (ES); Jesús Prieto Valtueñ, Pamplona-Navarra (ES); Francisco Borrás Cuesta, Pamplona-Navarra (ES)

(73) Assignee: Proyecto de Biomedicina Cima, S.L., Navarra (ES)

( * ) Notice: Subject to any disclaimer, the term of this patent is extended or adjusted under 35 U.S.C. 154(b) by 0 days.

(21) Appl. No.: 12/593,321

(22) PCT Filed: Mar. 27, 2008

(86) PCT No.: PCT/ES2008/000181
§ 371 (c)(1),
(2), (4) Date: Sep. 28, 2009

(87) PCT Pub. No.: WO2008/116956
PCT Pub. Date: Oct. 2, 2008

(65) Prior Publication Data
US 2010/0168015 A1    Jul. 1, 2010

(30) Foreign Application Priority Data
Mar. 27, 2007    (ES) .................... 200700806

(51) Int. Cl.
*C12N 15/00*    (2006.01)
*C12N 5/00*    (2006.01)
*A61K 38/10*    (2006.01)
*A61K 31/70*    (2006.01)
*C07K 7/08*    (2006.01)

(52) U.S. Cl. .................... 514/21.5; 435/320.1; 435/325; 536/23.1; 530/326; 514/44 R

(58) Field of Classification Search .................... None
See application file for complete search history.

(56) References Cited

FOREIGN PATENT DOCUMENTS

| EP | 0724016 A1 | 1/1996 |
|---|---|---|
| JP | 08151396 A | 6/1996 |
| JP | 10237098 A | 9/1998 |
| WO | 9735194 A | 9/1997 |
| WO | 2006031727 A2 | 3/2006 |
| WO | 2006119170 A2 | 11/2006 |

OTHER PUBLICATIONS

Teijin Ltd., Human Leucocyte Antigen DQ4 Binding Peptide #58, Database UniProt, Jun. 11, 1990, Database Accession No. AAW49167.

Teijin Ltd., Human Leucocyte Antigen DQ4 Binding Peptide #52, Database UniProt, Jun. 11, 1996, Database Accession No. AAW49161.

Jolivet-Reynaud C., Synthetic Library Peptide #6 Which Binds Anti-T. Gondii P30 Antibody, Database UniProt, Apr. 15, 1997, Database Accession No. AAW12281.

Immuno Japan Inc., Glycolipid Sugar Chain Replica Peptide #LC012, Database UniProt, Nov. 26, 1998, Database Accession No. AAW71348.

Teijin Ltd., Human Leucocyte Antigen DQ4 Binding Peptide #81, Database UniProt, Jun. 5, 1998, Database Accession No. AAW49190.

Chouaib, Salem, et al., The host-tumor immune conflict: from immunosuppression to resistance and destruction, Immunology Today, Oct. 1, 1997, pp. 493-497 vol. 18, No. 10.

Vicari, Alain P., et al., Reversal of Tumor-induced Dendritic Cell Paralysis by CpG Immunostimulatory Oligonucleotide and Anti-Interleukin 10 Receptor Antibody, Journal of Experimental Medicine, Aug. 19, 2002, pp. 541-549, vol. 196, No. 4.

Larche, Mark, Peptide therapy for allergic diseases: basic mechanisms and new clinical approaches, Pharmacology & Therapeutics, 2005, pp. 353-361, vol. 108.

Rigopoulou, Eirini I., et al., Blocking of inerleukin-10 receptor—a novel approach to simulate T-helper cell type 1 responses to hepatitis C virus, Clinical Immunology, 2005, pp. 57-64, vol. 117.

*Primary Examiner* — Marianne P Allen
(74) *Attorney, Agent, or Firm* — Andrew D. Gerschutz; Tristan A. Fuierer; Moore & Van Allen, PLLC

(57) ABSTRACT

The invention relates to peptides having the capacity to bind to interleukin-10 (IL-10) and their use in the treatment of clinical conditions or pathological disorders associated to IL-10 expression, particularly to a high IL-10 expression, for example, infectious diseases, tumors, cancers and acute damage conditions.

13 Claims, 12 Drawing Sheets

A

B

SEQUENCE LISTING

```
<160> NUMBER OF SEQ ID NOS: 54

<210> SEQ ID NO 1
<211> LENGTH: 15
<212> TYPE: PRT
<213> ORGANISM: Artificial
<220> FEATURE:
<223> OTHER INFORMATION: Synthetic Construct

<400> SEQUENCE: 1

Arg Lys Leu Arg Pro His Trp Leu His Phe His Pro Val Ala Val
1               5                   10                  15

<210> SEQ ID NO 2
<211> LENGTH: 15
<212> TYPE: PRT
<213> ORGANISM: Artificial
<220> FEATURE:
<223> OTHER INFORMATION: Synthetic Construct

<400> SEQUENCE: 2

Ala Arg Trp Met His Arg His His Gly Trp Ser Asp Arg His Arg
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic Construct

<400> SEQUENCE: 3

Pro Phe Val Val Ser Asp Ile Ala Phe Met Gly Leu Phe Tyr Asp
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic Construct

<400> SEQUENCE: 4

Ala Lys Val Pro Ser Phe Arg Arg Ser Ser Leu Gly Ser Val Arg
1               5                   10                  15

<210> SEQ ID NO 5
```

```
<211> LENGTH: 15
<212> TYPE: PRT
<213> ORGANISM: Artificial
<220> FEATURE:
<223> OTHER INFORMATION: Synthetic Construct

<400> SEQUENCE: 5

Arg Phe Tyr His Ala Asp Met Leu Leu Arg His Val Leu Met Met
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic Construct

<400> SEQUENCE: 6

Cys His Arg Cys Phe His Phe Arg Arg His Pro Val Ala Val Phe
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic Construct

<400> SEQUENCE: 7

His Arg Trp Met Pro His Val Phe Ala Val Arg Gln Gly Ala Ser
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic Construct

<400> SEQUENCE: 8

Thr Arg His Arg His Val Pro Arg Phe Leu Pro Leu Arg His Val
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic Construct

<400> SEQUENCE: 9

Trp Ala Tyr Tyr His Ala Gly His Ser Ser Phe Ala Val Trp Thr
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthetic Construct

<400> SEQUENCE: 10

Gly Ala Gly Val Leu Thr Pro Phe Thr Trp Arg Arg Phe His Met
1               5                   10                  15

<210> SEQ ID NO 11
<211> LENGTH: 15
<212> TYPE: PRT
```

```
<213> ORGANISM: Artificial
<220> FEATURE:
<223> OTHER INFORMATION: Synthetic Construct

<400> SEQUENCE: 11

Arg Met Leu Gly Phe Met Ser Gly Ser Trp Arg Thr Pro Val Arg
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthetic Construct

<400> SEQUENCE: 12

Gly Val Leu Ser Ser Ile Phe Ser Trp Arg Leu Val Ala Leu His
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic Construct

<400> SEQUENCE: 13

Ile Phe Arg Val Leu Ser Arg Met Leu Pro Gly Thr Ser Val Ile
1               5                   10                  15

<210> SEQ ID NO 14
<211> LENGTH: 15
<212> TYPE: PRT
<213> ORGANISM: Artificial
<220> FEATURE:
<223> OTHER INFORMATION: Synthetic Construct

<400> SEQUENCE: 14

Ala Arg Phe Pro Lys Glu Leu Arg Gly Ser Val Arg Ser Ala His
1               5                   10                  15

<210> SEQ ID NO 15
<211> LENGTH: 15
<212> TYPE: PRT
<213> ORGANISM: Artificial
<220> FEATURE:
<223> OTHER INFORMATION: Synthetic Construct

<400> SEQUENCE: 15

Gly Arg Val Pro Ser Met Phe Gly Gly His Phe Phe Ser Arg
1               5                   10                  15

<210> SEQ ID NO 16
<211> LENGTH: 15
<212> TYPE: PRT
<213> ORGANISM: Artificial
<220> FEATURE:
<223> OTHER INFORMATION: Synthetic Construct

<400> SEQUENCE: 16

Trp Ser Leu Leu Arg Ile Val Tyr Asn Arg His Ser His Ser Lys
1               5                   10                  15

<210> SEQ ID NO 17
<211> LENGTH: 15
<212> TYPE: PRT
<213> ORGANISM: Artificial
<220> FEATURE:
```

<223> OTHER INFORMATION: Synthetic Construct

<400> SEQUENCE: 17

Arg Gly Trp Ile Leu Asp Val Val Tyr Leu Tyr Pro Gly Pro Leu
1               5                   10                  15

<210> SEQ ID NO 18
<211> LENGTH: 15
<212> TYPE: PRT
<213> ORGANISM: Artificial
<220> FEATURE:
<223> OTHER INFORMATION: Synthetic Construct

<400> SEQUENCE: 18

Phe Ser Trp Tyr Phe Arg His His Arg Leu Met Val Ala Gly Pro
1               5                   10                  15

<210> SEQ ID NO 19
<211> LENGTH: 15
<212> TYPE: PRT
<213> ORGANISM: Artificial
<220> FEATURE:
<223> OTHER INFORMATION: Synthetic Construct

<400> SEQUENCE: 19

Gly Arg Phe Arg His Tyr Ser Met Leu Arg His His Ser Ile Arg
1               5                   10                  15

<210> SEQ ID NO 20
<211> LENGTH: 15
<212> TYPE: PRT
<213> ORGANISM: Artificial
<220> FEATURE:
<223> OTHER INFORMATION: Synthetic Construct

<400> SEQUENCE: 20

His Gly Phe Phe Ala Gly Gly Leu Ala His Trp His Gly His Arg
1               5                   10                  15

<210> SEQ ID NO 21
<211> LENGTH: 15
<212> TYPE: PRT
<213> ORGANISM: Artificial
<220> FEATURE:
<223> OTHER INFORMATION: Synthetic Construct

<400> SEQUENCE: 21

Ala His Arg Cys Cys His Leu Phe Thr Leu Ala Phe Leu Phe Ala
1               5                   10                  15

<210> SEQ ID NO 22
<211> LENGTH: 15
<212> TYPE: PRT
<213> ORGANISM: Artificial
<220> FEATURE:
<223> OTHER INFORMATION: Synthetic Construct

<400> SEQUENCE: 22

Phe Arg Ser Phe His Tyr His Thr Gly Arg Trp His Trp Leu Pro
1               5                   10                  15

<210> SEQ ID NO 23
<211> LENGTH: 15
<212> TYPE: PRT
<213> ORGANISM: Artificial
<220> FEATURE:
<223> OTHER INFORMATION: Synthetic Construct

```
<400> SEQUENCE: 23

Glu Ser Phe Phe Val Cys Ala Gly Leu Cys Arg Leu Gln Pro Tyr
1               5                   10                  15

<210> SEQ ID NO 24
<211> LENGTH: 15
<212> TYPE: PRT
<213> ORGANISM: Artificial
<220> FEATURE:
<223> OTHER INFORMATION: Synthetic Construct

<400> SEQUENCE: 24

Leu Phe Leu Leu Ser Gly Val Phe Val Pro Asp Leu His Glu Gly
1               5                   10                  15

<210> SEQ ID NO 25
<211> LENGTH: 15
<212> TYPE: PRT
<213> ORGANISM: Artificial
<220> FEATURE:
<223> OTHER INFORMATION: Synthetic Construct

<400> SEQUENCE: 25

His Arg His Phe Arg Trp Leu Asn Gly Met Pro Arg Leu Leu Gly
1               5                   10                  15

<210> SEQ ID NO 26
<211> LENGTH: 15
<212> TYPE: PRT
<213> ORGANISM: Artificial
<220> FEATURE:
<223> OTHER INFORMATION: Synthetic Construct

<400> SEQUENCE: 26

Gly Cys Ser Ala Leu Val Gly Phe Leu Ile Leu Leu Cys Cys Met
1               5                   10                  15

<210> SEQ ID NO 27
<211> LENGTH: 18
<212> TYPE: DNA
<213> ORGANISM: Artificial
<220> FEATURE:
<223> OTHER INFORMATION: Synthetic Construct

<400> SEQUENCE: 27
agccctcata gttagcgt                                            18

<210> SEQ ID NO 28
<211> LENGTH: 17
<212> TYPE: PRT
<213> ORGANISM: Artificial
<220> FEATURE:
<223> OTHER INFORMATION: Synthetic Construct

<400> SEQUENCE: 28

Leu Pro Asn Met Leu Arg Asp Leu Arg Asp Ala Phe Ser Arg Val Lys
1               5                   10                  15

Thr

<210> SEQ ID NO 29
<211> LENGTH: 25
<212> TYPE: PRT
<213> ORGANISM: Artificial
<220> FEATURE:
<223> OTHER INFORMATION: Synthetic Construct

<400> SEQUENCE: 29
```

```
Asp Ile Lys Ala His Val Asn Ser Leu Gly Glu Asn Leu Lys Thr Leu
1               5                   10                  15

Arg Leu Arg Leu Arg Arg Cys His Arg
            20                  25

<210> SEQ ID NO 30
<211> LENGTH: 12
<212> TYPE: PRT
<213> ORGANISM: Artificial
<220> FEATURE:
<223> OTHER INFORMATION: Synthetic Construct

<400> SEQUENCE: 30

Asp Ile Lys Ala His Val Asn Ser Leu Gly Glu Asn
1               5                   10

<210> SEQ ID NO 31
<211> LENGTH: 12
<212> TYPE: PRT
<213> ORGANISM: Artificial
<220> FEATURE:
<223> OTHER INFORMATION: Synthetic Construct

<400> SEQUENCE: 31

Lys Val Arg Ser Phe Ala Asp Arg Leu Asp Arg Leu
1               5                   10

<210> SEQ ID NO 32
<211> LENGTH: 12
<212> TYPE: PRT
<213> ORGANISM: Artificial
<220> FEATURE:
<223> OTHER INFORMATION: Synthetic Construct

<400> SEQUENCE: 32

Leu Arg Asp Leu Arg Asp Ala Phe Ser Arg Val Lys
1               5                   10

<210> SEQ ID NO 33
<211> LENGTH: 12
<212> TYPE: PRT
<213> ORGANISM: Artificial
<220> FEATURE:
<223> OTHER INFORMATION: Synthetic Construct

<400> SEQUENCE: 33

Leu Asp Arg Leu Asp Arg Ala Phe Ser Asp Val Asp
1               5                   10

<210> SEQ ID NO 34
<211> LENGTH: 12
<212> TYPE: PRT
<213> ORGANISM: Artificial
<220> FEATURE:
<223> OTHER INFORMATION: Synthetic Construct

<400> SEQUENCE: 34

Asp Val Asp Ser Phe Ala Arg Asp Leu Arg Asp Leu
1               5                   10

<210> SEQ ID NO 35
<211> LENGTH: 9
<212> TYPE: PRT
<213> ORGANISM: Artificial
<220> FEATURE:
<223> OTHER INFORMATION: Synthetic Construct
```

```
<400> SEQUENCE: 35

Asp Thr Leu Asp Leu Asp Leu Asp Asp
1               5

<210> SEQ ID NO 36
<211> LENGTH: 9
<212> TYPE: PRT
<213> ORGANISM: Artificial
<220> FEATURE:
<223> OTHER INFORMATION: Synthetic Construct

<400> SEQUENCE: 36

Asp Asp Leu Asp Leu Asp Leu Thr Asp
1               5

<210> SEQ ID NO 37
<211> LENGTH: 13
<212> TYPE: PRT
<213> ORGANISM: Artificial
<220> FEATURE:
<223> OTHER INFORMATION: Synthetic Construct

<400> SEQUENCE: 37

Phe Ile Ser Glu Ala Ile Ile His Val Leu His Ser Arg
1               5                   10

<210> SEQ ID NO 38
<211> LENGTH: 13
<212> TYPE: PRT
<213> ORGANISM: Artificial
<220> FEATURE:
<223> OTHER INFORMATION: Synthetic Construct

<400> SEQUENCE: 38

Phe Ile Gly Glu Ala Ile Ile His Val Leu His Ser Arg
1               5                   10

<210> SEQ ID NO 39
<211> LENGTH: 13
<212> TYPE: PRT
<213> ORGANISM: Artificial
<220> FEATURE:
<223> OTHER INFORMATION: Synthetic Construct

<400> SEQUENCE: 39

Phe Ile Ser Glu Ala Ile Ile Lys Val Leu His Ser Arg
1               5                   10

<210> SEQ ID NO 40
<211> LENGTH: 15
<212> TYPE: PRT
<213> ORGANISM: Artificial
<220> FEATURE:
<223> OTHER INFORMATION: Synthetic Construct

<400> SEQUENCE: 40

Glu Ser Gln Ala Val His Ala Ala His Ala Glu Ile Asn Glu Ala
1               5                   10                  15

<210> SEQ ID NO 41
<211> LENGTH: 15
<212> TYPE: PRT
<213> ORGANISM: Artificial
<220> FEATURE:
<223> OTHER INFORMATION: Synthetic Construct

<400> SEQUENCE: 41
```

-continued

Gly Ser Gln Ala Val His Ala Ala His Ala Glu Ile Asn Glu Ala
1               5                   10                  15

<210> SEQ ID NO 42
<211> LENGTH: 15
<212> TYPE: PRT
<213> ORGANISM: Artificial
<220> FEATURE:
<223> OTHER INFORMATION: Synthetic Construct

<400> SEQUENCE: 42

Lys Ser Gln Ala Val His Ala Ala His Ala Glu Ile Asn Glu Ala
1               5                   10                  15

<210> SEQ ID NO 43
<211> LENGTH: 15
<212> TYPE: PRT
<213> ORGANISM: Artificial
<220> FEATURE:
<223> OTHER INFORMATION: Synthetic Construct

<400> SEQUENCE: 43

Arg Gly Trp Ile Lys Asp Val Val Tyr Leu Tyr Pro Gly Pro Leu
1               5                   10                  15

<210> SEQ ID NO 44
<211> LENGTH: 15
<212> TYPE: PRT
<213> ORGANISM: Artificial
<220> FEATURE:
<223> OTHER INFORMATION: Synthetic Construct

<400> SEQUENCE: 44

Arg Gly Trp Ile Arg Asp Val Val Tyr Leu Tyr Pro Gly Pro Leu
1               5                   10                  15

<210> SEQ ID NO 45
<211> LENGTH: 14
<212> TYPE: PRT
<213> ORGANISM: Artificial
<220> FEATURE:
<223> OTHER INFORMATION: Synthetic Construct

<400> SEQUENCE: 45

His Arg Cys Phe His Phe Arg Arg His Pro Val Ala Val Phe
1               5                   10

<210> SEQ ID NO 46
<211> LENGTH: 14
<212> TYPE: PRT
<213> ORGANISM: Artificial
<220> FEATURE:
<223> OTHER INFORMATION: Synthetic Construct

<400> SEQUENCE: 46

Cys His Arg Cys Phe His Phe Arg Arg His Pro Val Ala Val
1               5                   10

<210> SEQ ID NO 47
<211> LENGTH: 13
<212> TYPE: PRT
<213> ORGANISM: Artificial
<220> FEATURE:
<223> OTHER INFORMATION: Synthetic Construct

<400> SEQUENCE: 47

Cys His Arg Cys Phe His Phe Arg Arg His Pro Val Ala
1               5                   10

```
<210> SEQ ID NO 48
<211> LENGTH: 13
<212> TYPE: PRT
<213> ORGANISM: Artificial
<220> FEATURE:
<223> OTHER INFORMATION: Synthetic Construct

<400> SEQUENCE: 48

His Arg Cys Phe His Phe Arg Arg His Pro Val Ala Val
1               5                   10

<210> SEQ ID NO 49
<211> LENGTH: 12
<212> TYPE: PRT
<213> ORGANISM: Artificial
<220> FEATURE:
<223> OTHER INFORMATION: Synthetic Construct

<400> SEQUENCE: 49

His Arg Cys Phe His Phe Arg Arg His Pro Val Ala
1               5                   10

<210> SEQ ID NO 50
<211> LENGTH: 12
<212> TYPE: PRT
<213> ORGANISM: Artificial
<220> FEATURE:
<223> OTHER INFORMATION: Synthetic Construct

<400> SEQUENCE: 50

Arg Cys Phe His Phe Arg Arg His Pro Val Ala Val
1               5                   10

<210> SEQ ID NO 51
<211> LENGTH: 15
<212> TYPE: PRT
<213> ORGANISM: Artificial
<220> FEATURE:
<223> OTHER INFORMATION: Synthetic Construct

<400> SEQUENCE: 51

Cys His Arg Cys Phe His Phe Arg Arg His Pro Val Ala Val Ala
1               5                   10                  15

<210> SEQ ID NO 52
<211> LENGTH: 15
<212> TYPE: PRT
<213> ORGANISM: Artificial
<220> FEATURE:
<223> OTHER INFORMATION: Synthetic Construct

<400> SEQUENCE: 52

Cys His Arg Cys Phe His Phe Arg Arg His Pro Val Ala Ala Phe
1               5                   10                  15

<210> SEQ ID NO 53
<211> LENGTH: 13
<212> TYPE: PRT
<213> ORGANISM: Artificial
<220> FEATURE:
<223> OTHER INFORMATION: Synthetic Construct

<400> SEQUENCE: 53

Ser His Arg Cys Phe His Phe Arg Arg His Pro Val Ala
1               5                   10
```

```
<210> SEQ ID NO 54
<211> LENGTH: 15
<212> TYPE: PRT
<213> ORGANISM: Artificial
<220> FEATURE:
<223> OTHER INFORMATION: Synthetic Construct

<400> SEQUENCE: 54

Asn Asn Thr Arg Lys Arg Ile Arg Ile Gln Arg Gly Pro Gly Arg
1               5                   10                  15
```

PEPTIDES WITH CAPACITY FOR BINDING WITH INTERLEUKINE 10 (IL-10)

CROSS-REFERENCE TO RELATED APPLICATIONS

This application is filed under the provisions of 35 U.S.C. §371 and claims the priority of International Patent Application No. PCT/ES2008/000181 filed on 27 Mar. 2008 entitled "Peptides with Capacity for Binding with Interleukine 10 (IL-10)" in the name of Lorea Manterola Careaga, et al., which claims priority of Spanish Patent Application No. P200700806 filed on 27 Mar. 2007, both of which are hereby incorporated by reference herein in their entirety.

FIELD OF THE INVENTION

The invention generally relates to peptides having the capacity to bind to interleukin-10 (IL-10) and to their applications. The invention particularly relates to peptides inhibiting the biological activity of IL-10 by means of their direct binding to IL-10, and to their use in the treatment of clinical conditions or pathological disorders associated to IL-10 expression, particularly to a high IL-10 expression.

BACKGROUND OF THE INVENTION

Immune response includes both a cell response and a humoral response. Cell response is mostly mediated by T cells, whereas humoral response is mediated by B cells. Lymphocytes have important roles in immune response, including directing the cell death of cells infected by viruses, cytokine and antibody production, etc. Lymphocytes are also involved in acute and chronic inflammatory diseases.

Cytokines are soluble proteins mediating reactions between cells and affecting cell growth and differentiation. Cytokines exert their effects through the binding to specific receptors which leads to the activation of specific transduction signals for said cytokines.

Interleukin-10 (IL-10) is a pleiotropic cytokine produced by several cell types such as macrophages, monocytes, Th2 type and regulatory T cells and B cells. IL-10 is a cytokine with immunosuppressive and anti-inflammatory properties; it regulates a number of cellular myeloid and lymphoid activities and directly inhibits the production of several inflammatory cytokines by T cells and NK (Natural Killer) cells.

IL-10 was first described as a cytokine synthesis inhibitory factor (CSIF) produced by Th2 cells which inhibited production of proinflammatory cytokines such as interferon-gamma (IFN-γ), interleukin-1-alpha (IL-1α), interleukin-1-beta (IL-1β), interleukin-2 (IL-2) and tumor necrosis factor alpha (TNF-α), by Th1 cells. In addition to inhibiting production of proinflammatory cytokines, it has been shown that IL-10 can inhibit antigen-specific Th1 cell proliferation reducing the capacity of antigen-presenting monocytes through the deregulation of the major histocompatibility complex (MHC) class II expression in these cells.

The discovery that IL-10 has a strong inhibitory effect on Th1 cell activation and on production of proinflammatory cytokines led to the hypothesis that IL-10 was a potent immunosuppressant of cell-mediated immune responses. Other authors have proposed the use of this cytokine in the treatment of acute and chronic inflammatory processes as well as in autoimmune diseases. For these reasons, this cytokine has been used in several autoimmune diseases, such as psoriasis, rheumatoid arthritis and Crohn's disease. However, in other diseases, such as in infectious processes or in cancer, it has a negative effect since it prevents the induction of Th1 responses which would favor the cure. Examples of these processes include leprosy, tuberculosis, leishmaniasis, as well as viral infections. Thus, it has been described that IL-10 is abundantly expressed in chronic infection due to the hepatitis C virus (HCV). This cytokine can be produced by Th2 cells as a result of stimulating with HCV antigens. It can also be produced by regulatory T cells (CD4 and CD8) inhibiting the development of Th1 type antiviral effector cells. Finally, infected dendritic cells (DC) or monocytes in contact with HCV proteins produce a larger amount of IL-10 than non-infected cells, which favors the development of Th2 responses and prevents the elimination of the virus.

As mentioned above, another field in which IL-10 has an important role is in antitumor response. Thus, tumor cells or tumor infiltrate cells can produce, among other molecules, IL-10, which damages the functioning of DCs. Good DC functioning inhibition in tumors would be one of the reasons for which an antitumor response does not occur. Given that the inhibition of IL-10 in vitro and in vivo results in an increase in interleukin 12 (IL-12) production and, concomitantly, an increase in Th1 response, said IL-10 inhibition would be very useful both in certain antiviral therapies, such as chronic HCV infection, and in antitumor therapies, where potent Th1 type responses are to be induced. Thus, it has been described that the combination of a non-methylated oligonucleotide (CpG) and an anti-IL-10 receptor antibody, preventing the interaction between IL-10 and its receptor, allows inducing a more effective antitumor response, greater than that reached when only CpG is used (Vicari A. P. et al. Reversal of tumor-induced dendritic cell paralysis by CpG immuno-stimulatory oligonucleotide and anti-interleukin 10 receptor antibody. *J Exp Med*. Aug. 19, 2002; 196(4):541-9). Other strategies that are usually used to inhibit the biological activity of IL-10 include either the use of specific neutralizing antibodies or the use of antisense oligonucleotides (oligos) of the IL-10-encoding gene which block its expression. The use of antibodies allows a total and specific blockage of this cytokine (IL-10) although certain side-effects are enhanced both due to the presence of exogenous immunoglobulins in blood and due to the effects derived from the systemic blockage of IL-10. Furthermore, the stability of immunoglobulins over time does not allow a short time period control of the blockage of the activity of this cytokine. Antisense oligos inhibit IL-10 production at the gene expression level, which can generate important deregulations in all the processes in which this cytokine is involved.

It is therefore necessary to identify new IL-10 inhibitors which are specific, have a greater efficacy and are potentially useful in human therapy.

SUMMARY OF THE INVENTION

The invention is generally faced with the problem of searching for new compounds which can inhibit the biological activity of IL-10.

The solution provided by the present invention is based on the fact that the inventors have identified peptides which can not only bind to IL-10 but can also inhibit the biological activity of IL-10 by means of their direct binding to IL-10 itself. These peptides have been identified by means of using the technology associated to phage libraries which allows determining peptides with a size typically comprised between 6 and 15 amino acids having a high-affinity binding with IL-10, subsequently quantifying, by means of in vitro assays, the capacity to inhibit the biological activity of IL-10 of the different peptides.

The peptides which can bind to IL-10, particularly those which can inhibit the biological activity of IL-10 by means of their direct binding to IL-10, are potentially useful for the treatment of clinical conditions and pathological disorders associated to IL-10 expression, particularly to a high IL-10 expression. Likewise, the peptides which can bind to IL-10 provide a tool for studying the biological role of IL-10.

Therefore, one aspect of this invention relates to peptides having the capacity to bind to IL-10. In a particular and preferred embodiment, said peptides further have the capacity to inhibit the biological activity of IL-10.

In another aspect, the invention relates to a pharmaceutical composition comprising at least one of said peptides.

In another aspect, the invention relates to said peptides for the treatment of clinical conditions and pathological disorders associated to IL-10 expression, particularly to a high IL-10 expression.

In another aspect, the invention relates to the use of said peptides in the preparation of a medicinal product for the treatment of clinical conditions and pathological disorders associated to IL-10 expression, particularly to a high IL-10 expression.

In another aspect, the invention relates to DNA sequences encoding said peptides.

In another aspect, the invention relates to a DNA construct comprising a DNA sequence encoding a peptide provided by this invention.

In another aspect, the invention relates to a vector comprising said DNA sequence or said DNA construct.

In another aspect, the invention relates to a host cell, such as a transformed host cell, comprising said DNA sequence or DNA construct or said vector.

In another aspect, the invention relates to a process for producing a peptide provided by this invention which comprises culturing said host cells under conditions allowing the expression of said peptide and, if desired, the recovery of the peptide obtained.

In another aspect, the invention relates to said DNA sequences and DNA constructs for the treatment of clinical conditions and pathological disorders associated to IL-10 expression, particularly to a high IL-10 expression.

In another aspect, the invention relates to the use of said DNA sequences and DNA constructs in the preparation of vectors and cells for the treatment of clinical conditions or pathological disorders associated to IL-10 expression, particularly to a high IL-10 expression.

54). All of them were tested at a concentration of 200 µg/ml. The results shown correspond to the mean and deviations of two assays carried out in triplicate.

Figure 12:
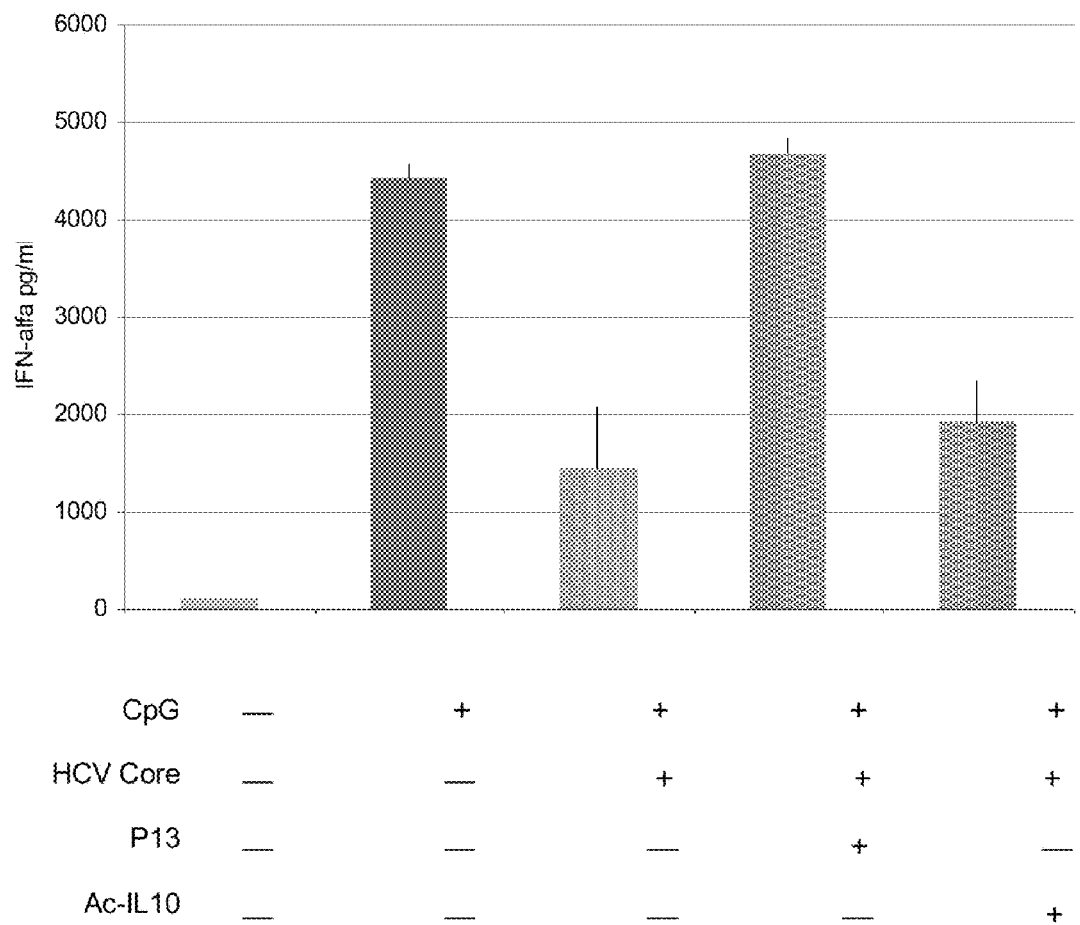

FIG. 12 is a bar graph showing the effect of peptide P13 (SEQ ID NO: 8) on IFN-α production in a peripheral blood mononuclear cell (PBMC) culture stimulated with a TLR9 ligand (CpG) and in the presence of the hepatitis C virus nucleocapsid (HCV core) protein. Briefly, PBMCs from healthy donors were stimulated with a TLR9 ligand (CpG, 5 µg/ml) with or without HCV core (2.5 µg/ml) and in the presence or absence of peptide P13 (SEQ ID NO: 8). An anti-IL-10 antibody (eBioscience, 16-7108-81) at a concentration of 1 µg/ml was used as a positive control. After 48 hours of incubation at 37° C. and 5% $CO_2$, IFN-α production in the supernatants of the culture was measured by means of ELISA. The results shown are representative of four experiments with similar results.

DETAILED DESCRIPTION OF THE INVENTION

The present invention generally relates to peptides with the capacity to bind to IL-10 and their applications.

Therefore, in one aspect, the invention relates to a peptide, hereinafter the peptide of the invention, with the capacity to bind to IL-10, selected from:

a) a peptide the amino acid sequence of which is selected from SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21; SEQ ID NO: 22; SEQ ID NO: 23; SEQ ID NO: 24; SEQ ID NO: 25; SEQ ID NO: 26; SEQ ID NO: 33; SEQ ID NO: 34; SEQ ID NO: 35 and SEQ ID NO: 36, b) a variant of a peptide defined in a); and c) a fragment of a peptide defined in a) or of a variant defined in b), comprising between 5 and 15 consecutive amino acids; and its pharmaceutically acceptable salts.

As used herein, the term "peptide" includes modifications or derivatives thereof, for example glycosylation, phosphorylation, acetylation, amidation, etc.

As used in the present description, the term "variant" relates to a peptide derived from a peptide as it has been previously defined in section a) in which an amino acid has been modified, by means of substitution for example, or which has insertions or deletions of one or more amino acids, with the condition that it conserves at least one of the functions of the original peptide, advantageously at least one function related to the binding to IL-10. Said variants normally comprise conservative substitutions, in which the function of the final peptide is not modified. Illustrative non-limiting examples of variants of peptide P9 (SEQ ID NO: 6) include peptides P9(15 Ala) (SEQ ID NO: 51), in which the amino acid in position 15 (Phe) of P9 (SEQ ID NO: 6) has been replaced by an Ala, peptide P9(14 Ala) (SEQ ID NO: 52), in which the amino acid in position 14 (Val) of P9 (SEQ ID NO: 6) has been replaced by an Ala, among others.

As used in the present description, the term "fragment" relates to a peptide derived from a peptide as it has been previously defined in a) or in b) in which an amino acid has been eliminated either from the amino end or from the carboxyl end or from both ends, maintaining one or more of the functions of the original peptide, preferably functions related to the binding to IL-10. Illustrative non-limiting examples of fragments of peptide P9 (SEQ ID NO: 6) include peptides P9(2-15) (SEQ ID NO: 45), P9(1-14) (SEQ ID NO: 46), P9(1-13) (SEQ ID NO: 47), P9(2-14) (SEQ ID NO: 48), P9(2-13) (SEQ ID NO: 49), P9(3-14) (SEQ ID NO: 50), P9(1-13; 1 Ser) (SEQ ID NO: 53), among others.

The pharmaceutically acceptable salts of the peptide of the invention are within the scope of this invention. As used herein, the term "pharmaceutically acceptable salts" includes the salts usually used to form metal salts or acid addition salts. The nature of the salt is not critical provided that it is pharmaceutically acceptable. The pharmaceutically acceptable salts of the peptide of the invention can be obtained from organic or inorganic acids or bases. Said salts can be obtained by conventional methods well known by persons skilled in the art.

The peptides of the invention have the capacity to bind to IL-10. Some of said peptides further have the capacity to inhibit the biological activity of IL-10 in vitro and/or in vivo.

The capacity of the peptides of the invention to bind to IL-10 can be determined by means of any suitable method which allows determining the binding between two molecules, by means of an affinity assay for example, which comprises placing IL-10 in contact with the peptide to be assayed under conditions allowing the binding of said peptide to IL-10 and evaluating the binding between the peptide and IL-10. In a particular embodiment, said affinity assay can be carried out using radioactively labeled IL-10 for example. Alternatively, the compound which can be labeled is the peptide to be assayed. This type of affinity assay generally comprises placing IL-10, immobilized in a plate blocked with streptavidin for example, in contact with the peptide the IL-10 binding capacity of which is to be known and after incubating for a suitable time period, analyzing the binding of the peptide to IL-10, as shown in Example 1 attached to the present description, The peptides with low affinity for IL-10 are eliminated by means of washes whereas the peptides with higher affinity remain bound to IL-10 and can be released by breaking the molecular interactions between both molecules, which can be carried out by decreasing the pH for example. By assaying the peptide against different concentrations of IL-10 or vice versa, an idea of the affinity of the peptide in question against IL-10 can be obtained.

Although all the peptides of the invention have the capacity to bind to IL-10, in a particular embodiment, the peptide of the invention with the capacity to bind to IL-10 is selected from the group consisting of the peptides identified as SEQ ID NO: 1, SEQ ID NO: 6, SEQ ID NO: 8, SEQ ID NO: 10, SEQ ID NO: 13, SEQ ID NO: 14, SEQ ID NO: 16, SEQ ID NO: 19, SEQ ID NO: 25, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52 and SEQ ID NO: 53, a variant or a fragment thereof, and their pharmaceutically acceptable salts.

The capacity of the peptides of the invention to inhibit the biological activity of IL-10 in vitro can be evaluated and, if desired, quantified by means of an assay for inhibiting the growth of the MC/9 cell line (CRL-8306, American Type Cell Culture (ATCC), Virginia, United States), a mastocyte cell line derived from rat liver the proliferation of which is induced by IL-10 (see Example 3).

In another particular embodiment, the peptide of the invention is a peptide with the capacity to inhibit the biological activity of IL-10 and is selected from the peptides identified as SEQ ID NO: 1 (P1); SEQ ID NO: 6 (P9); SEQ ID NO: 8 (P13); SEQ ID NO: 10 (P15); SEQ ID NO: 13 (P19); SEQ ID NO: 14 (P20); SEQ ID NO: 16 (P22); SEQ ID NO: 19 (P25) and SEQ ID NO: (P34), a variant or a fragment thereof, and their pharmaceutically acceptable salts. In addition to having the capacity to bind to IL-10 and inhibit the biological activity of IL-10, said peptides have common structural characteristics. Thus, said peptides (i) have in their amino acid sequence a percentage of hydrophobic amino acids (Ala, Val, Leu, Ile, Gly and Pro) and basic amino acids (Arg, His and Lys) between 60% and 90%, much greater than the expected percentage (about 45%); and (ii) have at least one aromatic amino acid, generally 2 or 3, selected from Phe, Trp and Tyr, preferably Phe. Likewise, as can be observed, an amino acid sequence alignment analysis, taking the peptide identified as SEQ ID NO: 8 (P13) as the reference peptide, shows the existence of a certain tendency to have basic amino acids (Arg, His, Lys) between position 2 to 5 and hydrophobic amino acids in positions 10 to 14, this pattern being maintained in the peptides identified as SEQ ID NO: 1 (P1), SEQ ID NO: 6 (P9), SEQ ID NO: 8 (P13), SEQ ID NO: 13 (P19) and SEQ ID NO: 25 (P34), this location being reversed for the peptides identified as SEQ ID NO: 10 (P15) and SEQ ID NO: 16 (P22) and being lost in the peptides identified as SEQ ID NO: 14 (P20) and SEQ ID NO: 19 (P25).

In a particular embodiment, the biomolecular interaction between human IL-10 and peptides P9 (SEQ ID NO: 6) and P13 (SEQ ID NO: 8), as well as of some derivatives thereof (truncated and/or modified forms) has been assayed by means of surface plasmon resonance (SPR) analysis, their capacity to bind to IL-10 being confirmed (Example 7). The inhibition exerted by peptides P9 (SEQ ID NO: 6) and P13 (SEQ ID NO: 8) has likewise been verified by means of their effect on STAT3 phosphorylation, which STAT3 molecule is involved in signaling after the binding of IL-10 to its cell receptor (Example 8). The effect of IL-10-inhibiting peptides provided by this invention has also been observed in an in vitro B16-F10 melanoma tumor cell proliferation assay (Example 9). Furthermore, as IL-10 is one of the negative factors which could determine the chronification of the infection due to hepatitis C virus (HCV), the efficacy of peptide P13 (SEQ ID NO: 8) has been tested in an in vitro model in which the HCV core protein (through its capacity to induce IL-10) is responsible for the low IFN-α production which is detected (Example 10); as can be observed in FIG. 12, said peptide P13 (SEQ ID NO: 8) can rescue IFN-α production.

For the initial identification of peptides with the capacity to bind to IL-10, the inventors have used the technology associated to phage libraries which allows determining peptides having a high affinity binding with IL-10, and subsequently quantifying by means of in vitro assays the capacity to inhibit the biological activity of IL-10 of different peptides. The sequence of the peptides binding to IL-10, inhibiting the biological activity of IL-10 in vitro, can be deduced from the corresponding DNA sequence after several biopanning cycles, generally 3. The use of phage libraries to identify inhibitors of certain products has been described, for example, by Chirinos-Rojas C. L. et al., in Immunology, 1999, January 96(1):109-113; McConnell S. J., et al., in Gene 1994, December 30, 151(1-2):115-118; or by Smith G. P., Science, Jun. 14, 1985, 228(4705):1315-1317.

Therefore, the invention provides a method for identifying peptides having the capacity to bind to IL-10 which comprises:
(i) using a phage library comprising a plurality of filamentous phages, the genome of each of said phages containing a nucleotide sequence encoding a different peptide linked to the gene of a phage coat protein, whereby each phage contains a different peptide genetically fused to a phage coat protein;
(ii) selecting, by means of an affinity assay, the phages containing the peptides binding with higher affinity to IL-10; and
(iii) determining the sequence of the peptides binding to IL-10 based on the corresponding DNA sequences inserted in the phages selected in step (ii) and encoding said peptides binding to IL-10

In a particular embodiment, for the purpose of obtaining peptides with a length of 15 amino acids which can bind with high affinity to IL-10 and with possible inhibitory activity for the biological activity of said cytokine, a phage library was used formed by a plurality of filamentous bacteriophages (M13), each of them containing a different peptide with 15 amino acids genetically fused to a phage coat protein, in this case bound to the N-terminal end of coat protein pIII. The phage thus has on its surface a peptide with 15 amino acids in each of the five molecules of the surface protein, whereas its inside contains the DNA encoding said peptide sequence. In the phage libraries, the peptide-encoding sequence comes from a sequence degenerated in each of the 15 positions with the 20 natural amino acids, which allows displaying $1.1 \times 10^{12}$ possible sequences of 15 amino acids in different phages. The physical ratio, 1 to 1, between the peptide sequence and the DNA encoding it in the bacteriophage allows selecting, from a large number of variants, the sequences binding specifically to IL-10. This process is carried out by means of an affinity assay.

In a particular embodiment, said affinity assay consists of an in vitro selection protocol called biopanning. Briefly, said technique consists of incubating a group of phages representing, for practical purposes, all the variants of peptides with 15 amino acids (in this case), in a plate blocked with streptavidin to which biotinylated IL-10 is added. The biotinylated IL-10 is anchored to the plate through the biotin-streptavidin interaction, whereby it is correctly displayed for its interaction with the peptides carried by the phages. After incubation, the unbound phages are eliminated by means of washes and subsequently the specifically bound phages are eluted by means of a pH decrease breaking the molecular interactions between IL-10 and the peptides displayed by the phages. The eluted phages are then amplified by means of infection in a bacterial strain. The process is repeated a total of 3 rounds, such that the content of phages binding specifically and with high affinity to IL-10 are enriched. The concentration of biotinylated IL-10 used to block the plates is progressively reduced in each round, for example from 2.5 to 0.02 µg/mL and, finally, 0.002 µg/mL. The phages selected in each round thus have a higher degree of affinity for IL-10. At the end of the process, the phages which have been selected for their affinity for IL-10 are sequenced with primers. This allows obtaining the sequences of the peptides displayed in the phages.

Example 1 attached to the present description shows the selection of peptides binding to IL-10 by means of a phage library, selection by the biopanning technique and sequencing of the peptides with a high affinity binding to IL-10. The peptides identified as SEQ ID NO: 1, SEQ ID NO: 2, SEQ ID NO: 3, SEQ ID NO: 4, SEQ ID NO: 5, SEQ ID NO: 6, SEQ ID NO 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21; SEQ ID NO: 22; SEQ ID NO: 23; SEQ ID NO: 24; SEQ ID NO: 25; and SEQ ID NO: 26, have been obtained by means of this technique.

In another particular case, for the initial identification of peptides with the capacity to bind to IL-10, the inventors have taken into account the structure of the (IL-10)-(IL-10 Receptor) complex (Josephson K, Logsdon N J, Walter M R. Crystal structure of the IL-10/IL-10R1 complex reveals a shared receptor binding site. *Immunity,* 2001 July; 15(1):35-46). By means of this approach (see Example 2), the inventors have observed that in said structure there are areas in IL-10 having an alpha helix conformation and oriented such that they could be considered relevant for the interaction of the cytokine with its receptor. Thus, the inventors have found that there are two alpha helix areas in IL-10, specifically, a first area comprising the 19-35 amino acid sequence of the IL-10 amino acid sequence and another second area comprising the 86-110 amino acid sequence of the IL-10 amino acid sequence which are oriented in an anti-parallel manner, therefore they can be considered possibly relevant in the interaction of the cytokine with its receptor. It is thus possible to identify areas of the IL-10 amino acid sequence which can be used in the synthesis of peptides with IL-10 inhibitory capacity, and subsequently quantify by means of in vitro assays the capacity to inhibit the biological activity of IL-10 of the different peptides as has been mentioned above.

Illustrative non-limiting examples of peptides with potential IL-10 inhibitory capacity identified by using the approach described above are shown in Table 2 (Example 2) and include the peptides identified as SEQ ID NO: 30 (F24), SEQ ID NO: 31 (F25), SEQ ID NO: 32 (F26), SEQ ID NO: 33 (F27), SEQ ID NO: 34 (F28), SEQ ID NO: 35 (F29) and SEQ ID NO: 36 (F30). As can be seen in said Table 2, the peptide identified as SEQ ID NO: 30 (F24) is a peptide comprising the 86-97 amino acid sequence of the native human IL-10 (hIL-10) amino acid sequence; the peptide identified as SEQ ID NO: 31 (F25) is a peptide comprising the 23-34 amino acid sequence of the native reverse hIL-10 amino acid sequence; the peptide identified as SEQ ID NO: 32 (F26) is a peptide comprising the 23-34 amino acid sequence of the native hIL-10 amino acid sequence; the peptide identified as SEQ ID NO: 33 (F27) is a peptide comprising the 23-34 amino acid sequence of the complementary native hIL-10 amino acid sequence and has the capacity to bind to IL-10; the peptide identified as SEQ ID NO: 34 (F28) is a peptide comprising the sequence of amino acids 23-34 of the complementary reverse native hIL-10 amino acid sequence and has the capacity to bind to IL-10; the peptide identified as SEQ ID NO: 35 (F29) is a peptide comprising the 99-107 amino acid sequence of the complementary native hIL-10 amino acid sequence and has the capacity to bind to IL-10, and the peptide identified as SEQ ID NO: 36 (F30) is a peptide comprising the sequence of amino acids 99-107 of the complementary reverse native hIL-10 amino acid sequence and has the capacity to bind to IL-10.

As used herein, the term "reverse" means that the amino acid sequence corresponds to the amino acid sequence of the protein or fragment of the native protein read in a reverse manner. As used herein, the term "complementary" relates to an amino acid sequence comprising residues which can "positively interact" with other complementary residues of the amino acid sequence of the native protein. As used herein, the term "positively interact" relates to situations in which the interaction between two amino acids generates attraction forces, either by electrostatic forces, hydrophobic interactions, hydrogen bonds, etc.

Due to the role of IL-10 in a number of biological processes, a result of the IL-10 inhibitory activity of the peptide of the invention is related to the potential development of a new family of drugs useful for the treatment of clinical conditions and pathological disorders associated to IL-10 expression, particularly to a high IL-10 expression, since such peptides allow blocking the excess of said cytokine originating the damage. The peptide of the invention would thus be potentially applicable in any clinical condition or pathological disorder in which an IL-10 increase is related to a worsening of the clinical condition of the subject or patient.

As used herein, the term "subject" relates to any member of a mammalian animal species and includes, but is not limited to domestic animals, primates and humans; the subject is preferably a male or female human being of any age or race.

The peptide of the invention can therefore be used in the treatment of clinical conditions or pathological disorders associated to IL-10 expression, particularly to a high IL-10 expression. Illustrative examples of said clinical conditions or pathological disorders which can be treated with the peptide of the invention where IL-10 has an immunosuppressive role include viral infections, bacterial infections, fungal infections, parasitic infections, tumors, cancers or acute damage conditions. In these types of infectious processes, tumors, cancers or acute damage conditions, IL-10 has a negative effect because it prevents the induction of Th1 responses which would favor the cure. Illustrative non-limiting examples of viral infections which can be treated with the peptide of the invention include virtually any infection of a viral origin, for example, infections caused by herpesviruses, for example, human herpesviruses such as herpes simplex virus type 1 (HSV-1), herpes simplex virus type 2 (HSV-2), varicella zoster virus (VZV), cytomegalovirus (CMV), human herpesvirus 6 (HHV-6), human herpesvirus 7 (HHV-7), Epstein-Barr virus (EBV), Kaposi's herpesvirus (HHV-8), etc., and optionally with their cutaneous reactivation after exposure to the sun, infections caused by hepatitis-causing viruses, for example the hepatitis C virus (HCV), etc. Illustrative non-limiting examples of bacterial infections which can be treated with the peptide of the invention include, but are not limited to infections caused by *Mycobacterium leprae*, infections caused by *Mycobacterium tuberculosis*, infections caused by *Yersinia pestis*, gastric infection caused by *Helicobacter pylori*, etc. Illustrative non-limiting examples of infections caused by fungi which can be treated with the peptide of the invention include, but are not limited to infections caused by *Candida albicans*, infections caused by *Trichophyton rubrum*, infections caused by *Aspergillus* sp., etc. Illustrative non-limiting examples of parasitic infections which can be treated with the peptide of the invention include, but are not limited to leishmaniasis, e.g., visceral leishmaniasis, infections caused by *Plasmodium falciparum*, toxoplasmosis, etc. Illustrative non-limiting examples of tumors and cancers which can be treated with the peptide of the invention include, but are not limited to Hodgkin's lymphoma, head and neck cancer, melanoma, basal cell carcinomas and squamous cell carcinomas developed from keratinocytes mutated by UV radiation, etc. Illustrative non-limiting examples of acute damage conditions which can be treated with the peptide of the invention include, but are not limited to burns and associated sepsis, etc. Generally any process of tumor development, viral, bacterial, fungal or parasitic infection in which the activity of IL-10 has a key immunosuppressive role in the aggravation or chronification of the clinical condition of a subject can be treated with the peptide of the invention.

Therefore, in another aspect, the invention relates to a pharmaceutical composition comprising a therapeutically effective amount of a peptide of the invention together with at least one pharmaceutically acceptable excipient. The pharmaceutical composition provided by this invention can contain one or more peptides of the invention together with, optionally, one or more alternative IL-10 inhibitor compounds. Said pharmaceutical composition is useful for its administration and/or application in the human or animal body, preferably in the human body. Virtually any IL-10 inhibitor compound other than the peptides of the invention can be present, if desired, in the pharmaceutical composition of the invention. Illustrative non-limiting examples of alternative IL-10 inhibitor compounds other than the peptides of the invention which can be used together with the peptide of the invention include, but are not limited to IFN-γ, AS101 ammonium trichloro(dioxoethylene-O,O') tellurate), neutralizing antibodies, 15d-PGD2 (15-deoxy-delta-12,14-prostaglandin J2), chimeric murine anti-human CD20 antibody (Ritubimax), etc.

The use of peptides such as the peptide of the invention, instead of using antisense oligonucleotides or antibodies, has a number of advantages because they are small molecules, with greater diffusion capacity and a shorter half-life. The peptides can have a high affinity for IL-10 but are degraded more quickly than antibodies, the adverse side-effects being able to be controlled by means of dosage. Carrying peptides to target organs or tissues is also easier compared to other types of compounds.

The peptide of the invention can be administered to treat the clinical conditions or the pathological disorders associated to IL-10 expression, particularly to a high (excess) IL-10 expression by any means causing the contact of the peptide of the invention with the site of action thereof in the human or animal body. The amount of peptide, derivative or pharmaceutically acceptable salt thereof which can be present in the pharmaceutical composition provided by this invention can vary within a wide range.

The dosage to treat a pathological disorder or disease associated to IL-10 expression, particularly to a high IL-10 expression, with the peptides and/or pharmaceutical compositions of the invention will depend on a number of factors, including the age, condition of the patient, the severity of the pathological disorder or disease, the route and frequency of administration and on the peptide of the invention to be administered.

The pharmaceutical compositions containing the peptide of the invention can be presented in any form of administration, solid or liquid for example, and can be administered by any suitable method, for example orally, parenterally, rectally or topically, for which the necessary pharmaceutically acceptable excipients for the formulation of the desired form of administration, for example ointments (lipogels, hydrogels, etc.), eye drops, sprays, injectable solutions, osmotic pumps, etc., will be included. A reviews of the different dosage forms of administration of medicinal products and of the necessary excipients for obtaining them can be found, for example, in the "Tratado de Farmacia Galénica", C. Fauli i Trillo, 1993, Luzán 5, S. A. Ediciones, Madrid.

Therefore, in another aspect, the invention relates to a peptide of the invention for the treatment of clinical conditions or pathological disorders associated to IL-10 expression, particularly to a high IL-10 expression. In a particular embodiment, said clinical condition or pathological disorder is a clinical condition or pathological disorder presenting IL-10 expression, particularly a high IL-10 expression. In a particular embodiment, said clinical condition or pathological disorder presenting IL-10 expression, particularly a high IL-10 expression, comprises clinical conditions in which the Th1 cell response is inhibited. Illustrative examples of said clinical conditions or pathological disorders which can be treated include viral infections, bacterial infections, fungal infections, parasitic infections, tumors, cancers or acute damage situations as has been previously mentioned.

The use of the peptide of the invention in the preparation of said pharmaceutical composition is an additional aspect of this invention. Therefore, in another aspect, the invention relates to the use of a peptide of the invention in the preparation of a medicinal product for the treatment of clinical conditions or pathological disorders associated to IL-10 expression, particularly to a high IL-10 expression. In a particular embodiment, said clinical condition or pathological disorder is a clinical condition or pathological disorder presenting IL-10 expression, particularly a high IL-10 expression. In a particular embodiment, said clinical condition or pathological disorder presenting IL-10 expression, particularly a high IL-10 expression, comprises clinical conditions in which Th1 cell response is inhibited. Illustrative examples of said clinical conditions or pathological disorders which can be treated include viral infections, bacterial infections, fungal infections, parasitic infections, tumors, cancers or acute damage situations as has been previously mentioned.

Methods for measuring IL-10 expression levels in a sample are well known by persons skilled in the art. Thus, by way of a non-limiting illustration, said methods include, for example, measurements in serum, sputum or seminal fluid samples of IL-10 levels or concentration by means of the ELISA technique for example. Said technique allows quantifying the IL-10 levels in a sample compared to normal levels, i.e. compared to IL-10 levels in healthy individual samples.

The peptide of the invention can be obtained by conventional methods, for example by means of solid phase chemical synthesis techniques; purified by means of conventional methods, for example by means of high performance liquid chromatography (HPLC); and, if desired, it can be analyzed by means of conventional techniques, for example, by means of sequencing and mass spectroscopy, amino acid analysis, nuclear magnetic resonance, etc. By way of a non-limiting illustration, the peptide of the invention can be obtained by means of peptide synthesis according to conventional processes (Merrifield R B. J Am Chem Soc 1963; 85:2149-2154) using the Atherton Fmoc variant (Atherton, E., Logan, J. C. and Sheppard, R. C. 1989. Peptide synthesis II. Procedures for solid phase synthesis using N-fluorenyl methoxycarbonyl amino acids on polyamide supports. Synthesis of substance P and of acyl carrier protein 65-74 decapeptide. *J. Chem. Soc. Perkin Trans.* 1:538). The purity of the peptide obtained can be determined by means of reversed-phase HPLC chromatography and/or mass spectrometry, for example.

Alternatively, the peptide of the invention can be obtained by means of recombinant DNA technology. Therefore, in another aspect, the invention provides a DNA sequence encoding a peptide of the invention. Said DNA sequence can be easily deduced from the amino acid sequence of the peptide of the invention.

Said DNA sequence can be contained in a DNA construct. Therefore, in another aspect, the invention provides a DNA construct comprising a DNA sequence encoding a peptide of the invention. Said DNA construct can incorporate an operatively bound sequence regulating the expression of the DNA sequence encoding the peptide of the invention. The control sequences are sequences controlling and regulating transcription and, where appropriate, translation of the peptide of the invention, and include promoter, terminator sequences, etc., functional in transformed host cells comprising said DNA construct or sequence. In a particular embodiment, said expression control sequence is functional in bacteria. Advantageously, said DNA construct further comprises a marker or gene encoding a motif or phenotype which allows selecting the transformed host cell with said DNA construct. The DNA construct provided by this invention can be obtained by means of using techniques that are widely known in the state of the art [Sambrook et al., "Molecular cloning, a Laboratory Manual", $2^{nd}$ ed., Cold Spring Harbor Laboratory Press, N.Y., 1989 Vol. 1-3].

The DNA sequence or the DNA construct provided by this invention can be inserted in a suitable vector. Therefore, in another aspect, the invention relates to a vector, such as an expression vector comprising said DNA construct or sequence. The choice of the vector will depend on the host cell in which it will be subsequently introduced. By way of example, the vector in which said DNA sequence is introduced can be a plasmid or a vector which, when it is introduced in a host cell, is or is not integrated in the genome of said cell. Said vector can be obtained by conventional methods known by the persons skilled in the art [Sambrok et al., 1989, mentioned above].

In another aspect, the invention relates to a host cell, such as a transformed host cell, comprising a DNA sequence or a DNA construct provided by this invention or a vector as has been previously mentioned. Said cell can be a prokaryotic or eukaryotic cell.

In another aspect, the invention relates to a pharmaceutical composition comprising a DNA sequence provided by this invention, a DNA construct provided by this invention, a vector provided by this invention, or a host cell provided by this invention, and a pharmaceutically acceptable carrier. In a particular embodiment, said pharmaceutical composition comprises a DNA sequence provided by this invention or a DNA construct provided by this invention in a gene transfer vector, such as a viral or non-viral vector. Suitable viral vectors for putting this embodiment of the invention into practice include, but are not limited to adenoviral vectors, adeno-associated vectors, retroviral vectors, lentiviral vectors, alphavirus vectors, herpesvirus vectors, coronavirus-derived vectors, etc. Suitable non-viral type vectors for putting this embodiment of the invention into practice include, but are not limited to naked DNA, liposomes, polyamines, dendrimers, cationic glycopolymers, liposome-polycation complexes, proteins, receptor-mediated gene transfer systems, etc.

Therefore, in another aspect, the invention relates to a DNA sequence provided by this invention, or to a DNA construct provided by this invention, or to a vector provided by this invention, or to a host cell provided by this invention, for the treatment of clinical conditions or pathological disorders associated to IL-10 expression, particularly to a high IL-10 expression. In a particular embodiment, said clinical condition or pathological disorder is a clinical condition or pathological disorder presenting IL-10 expression, particularly a high IL-10 expression. In a particular embodiment, said clinical condition or pathological disorder presenting IL-10 expression, particularly a high IL-10 expression, comprises clinical conditions in which Th1 cell response is inhibited. Illustrative examples of said clinical conditions or pathological disorders which can be treated include viral infections, bacterial infections, fungal infections, parasitic infections, tumors, cancers or acute damage situations as has been previously mentioned.

In another aspect, the invention relates to the use of said DNA sequences and DNA constructs in the preparation of vectors and cells for the treatment of clinical conditions and pathological disorders associated to IL-10 expression, particularly to a high IL-10 expression. According to this aspect of the invention, said DNA construct or sequence is put into contact with a gene transfer vector, such as a viral or non-viral vector. Suitable viral vectors for putting this embodiment of the invention into practice include, but are not limited to adenoviral vectors, adeno-associated vectors, retroviral vectors, lentiviral vectors, alphavirus vectors, herpesvirus vectors, coronavirus-derived vectors, etc. Suitable non-viral vectors for putting this embodiment of the invention into practice include, but are not limited to naked DNA, liposomes, polyamines, dendrimers, cationic glycopolymers, liposome-polycation complexes, proteins, receptor-mediated gene transfer systems, etc.

In another aspect, the invention relates to a process for producing a peptide of the invention which comprises growing a host cell comprising the DNA construct, sequence or vector provided by this invention under conditions allowing the production of said peptide of the invention and, if desired, the recovery of said peptide of the invention. The conditions for optimizing the culture of said host cell will depend on the host cell used. If desired, the process for producing the peptide of the invention further includes the isolation and purification of said peptide.

The following examples illustrate the invention and must not be considered as limiting the scope thereof.

Example 1

Selection of Peptides Binding to IL-10 by Means of a Phage Library

Figure 1:
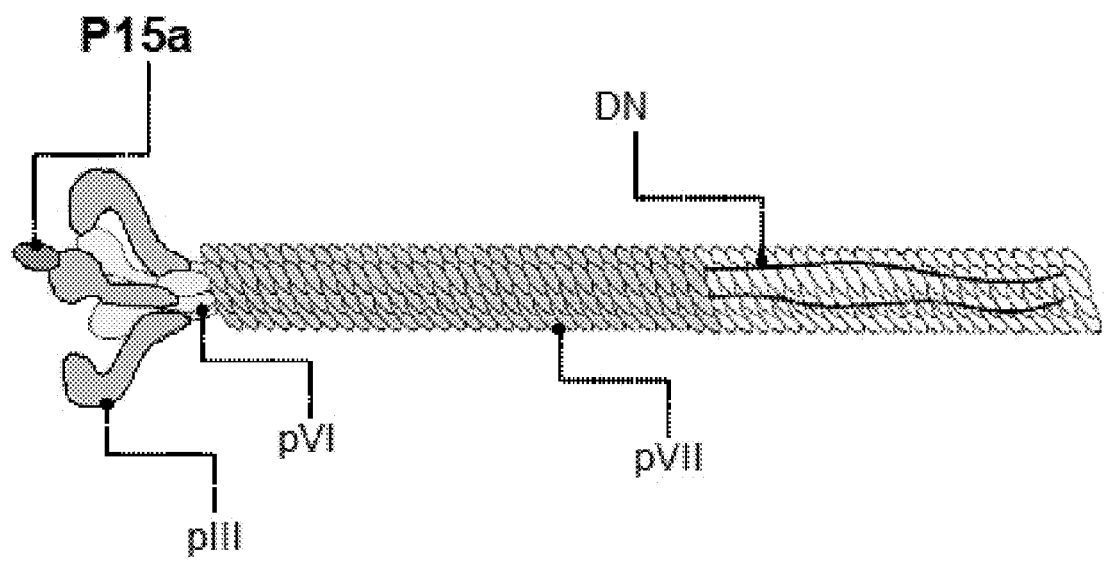
FIG. 1 schematically shows the position of a peptide with 15 amino acids (P15aa), genetically fused to protein pIII, on the surface of the filamentous bacteriophage M13.
Figure 2:
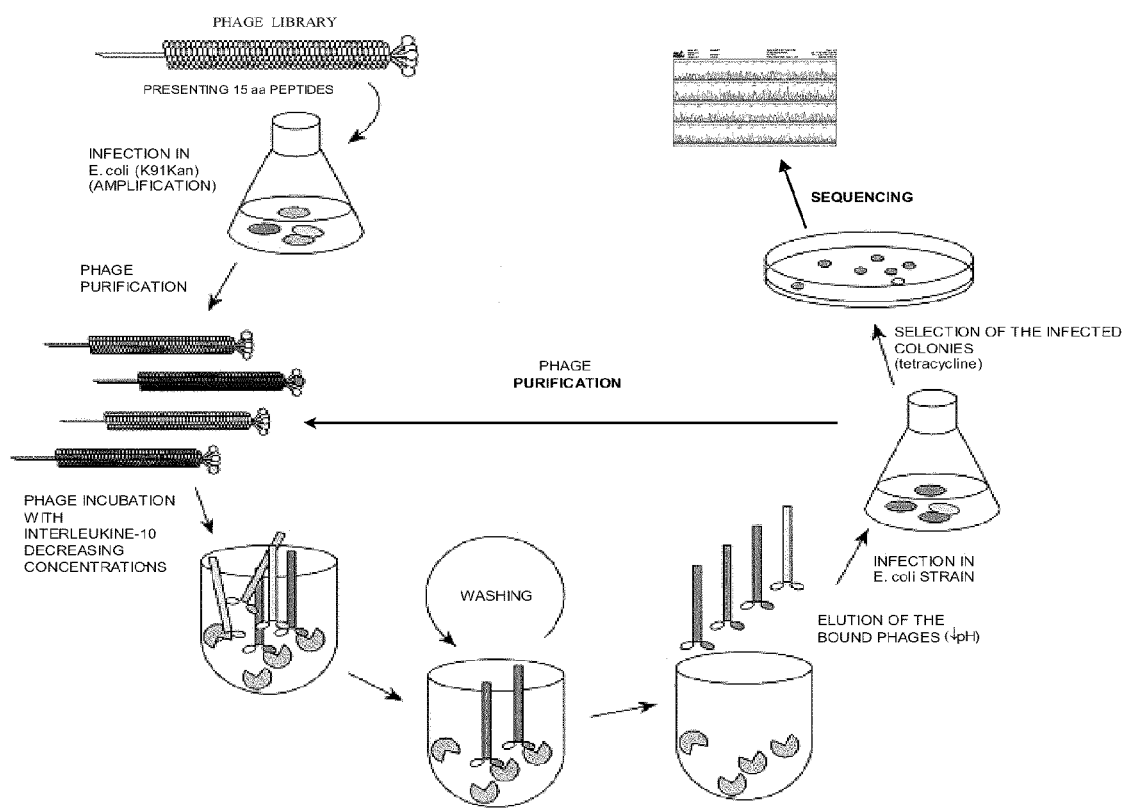
FIG. 2 schematically shows the selection of peptides by means of the biopanning technique. Biotinylated IL-10 is immobilized in plates containing streptavidin (through biotin-streptavidin binding). The phage library is screened based on the interaction between IL-10 and the peptides presented by the phages. The phages with low affinity for IL-10 are eliminated by means of washes. The phages retained in the plate are eluted by means of decreasing the pH. After three cycles of enriching phages with high affinity for IL-10, the phages are isolated and sequenced (see Example 1).

To obtain peptides with 15 amino acids which can bind with high affinity to IL-10 and with possible inhibitory activity for the biological activity of this cytokine, an in vitro selection technique based on the technology developed from phage libraries was used. These libraries consist of filamentous bacteriophages (M13) containing a peptide genetically fused to a virus coat protein, in this case bound to the N-terminal end of coat protein pIII (FIG. 1). The phage thus has on its surface a peptide with 15 amino acids in each of the 5 molecules of this protein that the phage has on its surface, whereas its inside contains the DNA encoding said peptide. In phage libraries, the peptide-encoding sequence comes from a sequence degenerated in each of the 15 positions with the 20 natural amino acids. This allows displaying $1.1 \times 10^{12}$ possible sequences of 15 amino acids in different phages. The physical ratio, 1 to 1, between the peptide sequence and the DNA encoding it in the bacteriophage allows selecting, from a large number of variants, the sequences binding specifically to IL-10. This process is carried out by means of an in vitro selection protocol called "biopanning".

The phage library used for performing this example contains $2 \times 10^8$ different clones and was donated by the laboratory of George P. Smith (University of Missouri, USA).

Selection Technique

Biopanning

First, before biopanning, 10 µl of the phage library were amplified using the *Escherichia coli* K91Kan strain (supplied by G. P. Smith, Division of Biological Sciences Tucker Hall. University of Missouri) as host strain and then purified by means of two precipitations with polyethylene glycol (PEG)/NaCl and a CsCl gradient centrifugation.

The titer of the phage suspension calculated by spectrometry was $3.82 \times 10^{14}$ virions/ml and the number of infectious particles was $1.3 \times 10^{13}$ TU/ml. Before starting with the selection assay, a fraction of this phage suspension was sequenced to verify that the amplification had not affected the clone diversity.

Figure 3:
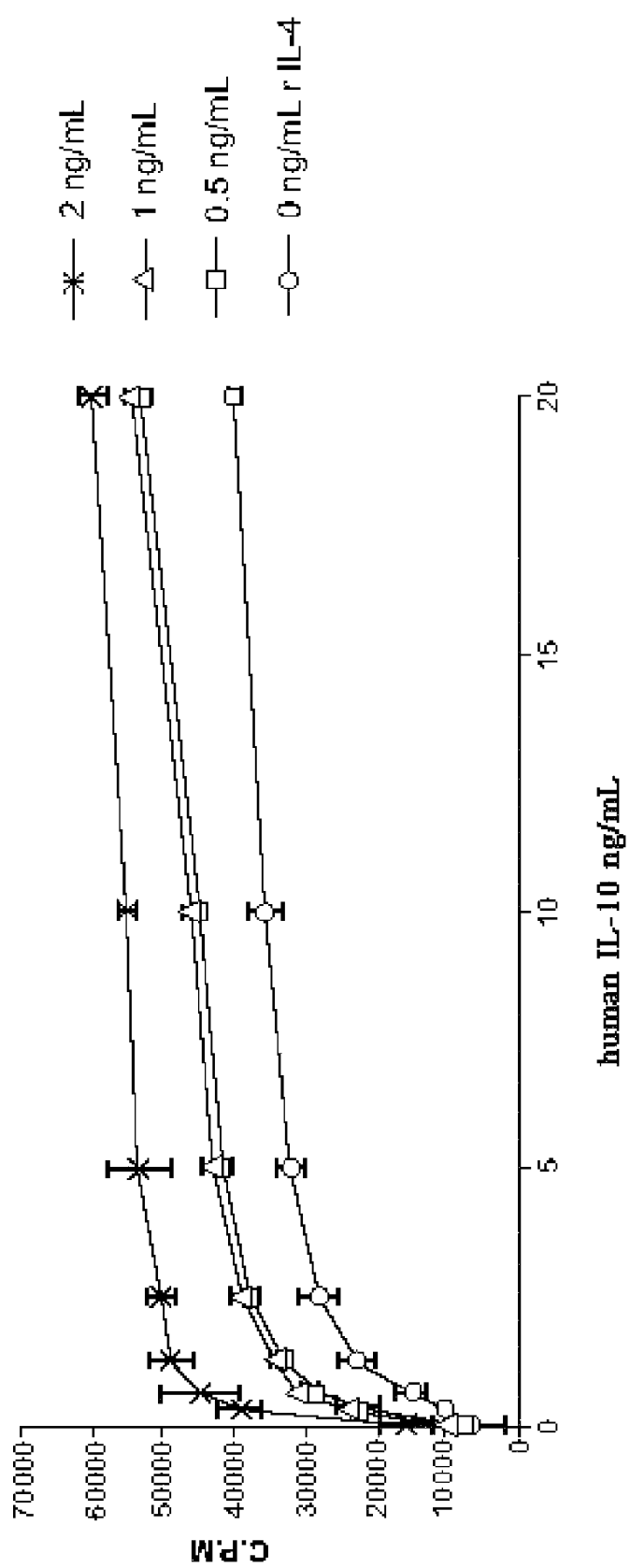
FIG. 3 is a graph showing MC/9 cell proliferation in the presence of different concentrations of human IL-10 and of mouse interleukin-4 (IL-4).

The biopanning technique consists of incubating a group of phages representing (for practical purposes) all the variants with 15 amino acids, in a plate blocked with streptavidin (10 µg/ml in 0.1 M NaHCO$_3$, 2 hours at room temperature) to which biotinylated IL-10 is added. The biotinylated IL-10 is anchored to the plate through the biotin-streptavidin interaction, whereby it is correctly displayed for its interaction with the peptides carried by the phages. IL-10 is put into contact with the peptides carried by the phages at a concentration of 3×10$^4$ viruses/ml and allowed to incubate for approximately 12 hours. After incubation, the unbound phages are eliminated by means of washes with PBS/Tween (phosphate-buffered saline/polyoxyalkylene derivatives of sorbitan fatty acid esters) and subsequently the specifically bound phages are eluted by means of a pH decrease (elution buffer) breaking the molecular interactions between IL-10 and the peptides displayed by the phages. The eluted phages are then amplified by means of infection in a bacterial strain (*E. coli* K91Kan). The process is repeated a total of 3 rounds, such that the content of phages binding specifically and with high affinity to IL-10 is enriched (FIG. 3). The concentration of biotinylated IL-10 used to block the plates is progressively reduced in each round from 2.5 µg/ml to 0.02 µg/ml, and, finally, to 0.002 µg/ml. The phages selected in each round thus have an increasingly higher degree of affinity for IL-10. At the end of the process, phages which have been selected for their affinity for IL-10 are sequenced with primers, after being isolated by means of tetracycline resistance provided by genetically modified phages after infecting *E. coli* cells. This allows obtaining the sequences of the peptides displayed in the phages of an obtained number of clones of isolated colonies. The number of times that a sequence corresponding to a peptide with 15 amino acids carried by each clone is repeated, of the total of sequenced clones gives an idea of the relative degree of affinity that said peptide with 15 amino acids has for IL-10.

Peptide Sequences

To obtain phage clones, obtained from biopanning, a selection in the presence of an antibiotic of bacterial colonies infected by these phages, the resistance of which is given by a tetracycline resistance gene present in the genome of the phages, is carried out. With this method, only colonies infected by bacteriophages grow. Each colony thus contains the genome of a single phage to which the sequence of a single peptide displayed on its surface corresponds.

From bacterial colonies infected by phages, derived from the last round of selection by biopanning, its DNA was extracted and the genome portion comprising the region corresponding to the peptides displayed in protein pIII of the phage was sequenced using the specific primer hybridizing close to this region identified by SEQ ID NO: 27. The sequences shown in Table 1, in which the number of colonies (clones) carried by said sequences is furthermore indicated, were thus obtained.

TABLE 1

Amino acid sequences from phages interacting with IL-10

| Peptide No. | SEQ ID NO: | No. of colonies |
|---|---|---|
| P1 | 1 | 25 |
| P2 | 2 | 29 |
| P5 | 3 | 2 |
| P7 | 4 | 1 |
| P8 | 5 | 1 |

TABLE 1-continued

Amino acid sequences from phages interacting with IL-10

| Peptide No. | SEQ ID NO: | No. of colonies |
|---|---|---|
| P9 | 6 | 3 |
| P10 | 7 | 2 |
| P13 | 8 | 2 |
| P14 | 9 | 4 |
| P15 | 10 | 3 |
| P16 | 11 | 3 |
| P18 | 12 | 3 |
| P19 | 13 | 2 |
| P20 | 14 | 1 |
| P21 | 15 | 1 |
| P22 | 16 | 1 |
| P23 | 17 | 1 |
| P24 | 18 | 2 |
| P25 | 19 | 1 |
| P26 | 20 | 1 |
| P29 | 21 | 1 |
| P31 | 22 | 1 |
| P32 | 23 | 1 |
| P33 | 24 | 1 |
| P34 | 25 | 1 |
| P35 | 26 | 1 |

The number of clones (colonies) of each sequence gives a relative idea of the degree of affinity between the peptides and IL-10, i.e., the larger the number of clones, the greater the binding affinity. However, the degree of affinity does not correspond to the capacity to block the activity of IL-10 since some of the most active peptides, e.g. the peptides identified as SEQ ID NO: 6 (P9) and SEQ ID NO: 17 (P23), provide 3 and 1 clones, respectively, whereas the peptide identified as SEQ ID NO: 2, providing 29 clones, is much less active in the inhibition assay (Example 3). Although there is no intention to be linked to any theory, this issue could be explained on the basis that the most active peptide would probably block the binding of IL-10 to its receptor.

Peptide Sequence Comparison

The obtained sequences were analyzed with a "translate tool" program available on the Internet, which allows deducing the amino acid sequences which were subsequently worked with. A total of 143 clones was sequenced, which allowed identifying 35 different peptides (P1-P35), of which 9 of said peptides (P3, P4, P6, P11, P12, P17, P27, P28 and P30) were also found in other biopanning assays with other proteins, therefore it was considered that they were not specific for the binding to IL-10 and, consequently, they could be discarded. These non-specific bindings can be due to interactions with some of the components present during the selection process (plastic, biotin, streptavidin, etc.) and/or to phage surface proteins.

Example 2

Peptide Design Based on the Structure of the Complex Between Human IL-10 (hIL-10) and its Receptor In this case, human IL-10 (hIL-10) inhibitors were developed taking into account the structure of the (hIL-10)-(hIL-10 receptor) complex. In said structure, there are two alpha helix areas in the primary structure of hIL-10 (amino acids 19-35 and amino acids 86-110) which are oriented in an anti-parallel manner and could be relevant in its interaction with the receptor. The sequences of these peptides are indicated below:

(SEQ ID NO: 28)
Leu Pro Asn Met Leu Arg Asp Leu Arg Asp Ala Phe

Ser Arg Val Lys Thr (amino acids 19-35 of hIL-10)

(SEQ ID NO: 29)
Asp Ile Lys Ala His Val Asn Ser Leu Gly Glu Asn

Leu Lys Thr Leu Arg Leu Arg Leu Arg Arg Cys His

Arg (amino acids 86-110 of hIL-10)

Based on these sequences, the inventors speculated that the peptides indicated below in Table 2 and having a modification at their C-terminal end (said end is amidated) could bind to areas of hIL-10 (or to areas of the hIL-10 receptor) and prevent the interaction between hIL-10 and its receptor. It was thus predicted that the peptides shown in Table 2 and identified as SEQ ID NO: 30, SEQ ID NO: 31 and SEQ ID NO: 32 will bind to the hIL-10 receptor whereas the peptides identified as SEQ ID NO: 33, SEQ ID NO: 34, SEQ ID NO: 35 and SEQ ID NO: 36 will bind to hIL-10.

TABLE 2

Peptides predicted as potential hIL-10 inhibitors

| Peptide no. | SEQ ID NO: | Amino acid sequences | Amino acids (hIL-10) |
|---|---|---|---|
| F24 | 30 | Asp Ile Lys Ala His Val Asn Ser Leu Gly Glu Asn | 86-97 |
| F25 | 31 | Lys Val Arg Ser Phe Ala Asp Arg Leu Asp Arg Leu | Rev 23-34 |
| F26 | 32 | Leu Arg Asp Leu Arg Asp Ala Phe Ser Arg Val Lys | 23-34 |
| F27 | 33 | Leu Asp Arg Leu Asp Arg Ala Phe Ser Asp Val Asp | comp 23-34 |
| F28 | 34 | Asp Val Asp Ser Phe Ala Arg Asp Leu Arg Asp Leu | Rev comp 23-34 |
| F29 | 35 | Asp Thr Leu Asp Leu Asp Leu Asp Asp | comp 99-107 |
| F30 | 36 | Asp Asp Leu Asp Leu Asp Leu Thr Asp | Rev comp 99-107 | rev: the peptide sequence is read in a reverse direction; and comp: the sequence has residues that are complementary, in other words, they can positively interact with the residues of the related sequence.

Thus, for example, the peptide defined as "comp 99-107" (SEQ ID NO: 35) the amino acid sequence of which is complementary to the amino acid sequence of the hIL-10 fragment comprised between amino acid 99 and amino acid 107 (peptide 99-107) since the amino acids Lys and Arg present in said peptide 99-107 (indicated below in bold print) could interact with the amino acids Asp (also indicated in bold print) of the predicted peptide and which has been designed as "comp 99-107":

(SEQ ID NO: 35)
99-107      Lys Thr Leu Arg Leu Arg Leu Arg Arg comp 99-107 Asp Thr Leu Asp Leu Asp Leu Asp Asp

Example 3

Inhibition of the In Vitro Biological Activity of IL-10 by Means of Peptides in Proliferation Assays with MC/9 Cells The MC/9 cell line (CRL-8306, American Type Cell Culture (ATCC), Virginia, United States) are mastocytes derived from mouse liver, they grow in suspension and their proliferation is induced by the presence of IL-10 exogenously added to the culture medium. For this reason, the inhibition of the effect of exogenous IL-10 by means of synthetic peptides inhibiting said cytokine reduces the growth of MC/9 cells, which allows measuring in vitro the IL-10 inhibitory activity of said peptides. In this assay, the proliferation is measured indirectly as the incorporation of tritiated thymidine during DNA synthesis.

The most suitable conditions for conducting this assay, when both the inhibition of human IL-10 (hIL-10) and of mouse IL-10 (mIL-10) is to be evaluated are the following. The MC/9 cells are added to 96-well plates at an initial density of 20,000 cells/well in complete medium: DMEM (BE-12-604F BioWhittaker) with 10% FBS (10270-106 Gibco), 50 μg/mL streptomycin and 50 U/mL penicillin (15140-122 Gibco), 2 mM glutamine (BE17-605E BioWhittaker) and 2-mercaptoethanol supplemented with 5% RAT-STIM (354115 Becton Dickinson) together with 0.5 ng/mL mouse IL-4 (Preprotech EC, London, United Kingdom) and 1.25 ng/mL hIL-10 (e-Bioscience) or mIL-10 (e-Bioscience) as appropriate, and they are incubated at 37° C. and 5% $CO_2$ for 24 hours. After that time, 1 μCi of methyl-$^3$H-thymidine (Amersham Life Science, Buckinghamshire, United Kingdom) per well is added and the plate is incubated for 12 more hours in the same conditions. Finally, the cells are harvested, the tritiated thymidine, incorporated in the DNA synthesis, being transferred to plates (UniFilter-96 GF/C®, Perkin Elmer) and the radioactivity is quantified, after adding scintillation liquid, in a scintillation counter (Top Count, Microplate Scintillation Counter, Packard) and it is quantified measuring the emission of counts per minute (cpm) of each well.

The peptide inhibition capacity is determined using different concentrations (150, 100 and 50 μg/ml) of each peptide to be assayed. The peptide solutions are incubated for 2 hours with 1.25 ng/ml hIL-10 or mIL-10 as appropriate, and then the MC/9 cells are added together with mouse IL-4, so that the final concentration of IL-4 is 0.5 ng/ml. The negative proliferation control consists of cells incubated with mouse IL-4 whereas the positive proliferation control consists of cells incubated with mouse IL-4 and IL-10. An anti-human IL-10 antibody (e-Bioscience) or anti-mouse IL-10 antibody (e-Bioscience), as appropriate, (3 ng/ml) is used as an inhibition control. Each peptide was analyzed in triplicate. Results are expressed as the percentage of inhibition calculated by means of the following formula:

% Inhibition=(cpm max−cpm exp)/(cpm max−cpm min)×100 wherein:
"cpm max" are the maximum counts per minute;
"cpm exp" are the experimental counts per minute with peptide; and
"cpm min" are the baseline counts per minute.
The assayed peptides (FIG. 4) were obtained by means of peptide synthesis according to conventional processes (Merrifield R B. J Am Chem Soc 1963; 85:2149-2154) using the Atherton Fmoc variant (Atherton, E., Logan, J. C. and Sheppard, R. C. 1989. Peptide synthesis II. Procedures for solid phase synthesis using N-fluorenylmethoxycarbonyl amino acids on polyamide supports. Synthesis of substance P and of acyl carrier protein 65-74 decapeptide. *J. Chem. Soc. Perkin Trans.* 1:538). The purity of the peptides was determined by means of reversed-phase high performance liquid chromatography (HPLC) and/or mass spectrometry. Only those peptides with a purity equal to or greater than 80% were tested in relation to their capacity to inhibit the activity of IL-10.

In order to measure the capacity of the peptides to inhibit IL-10, it is necessary for them to be in solution in the culture medium in which the proliferation assay with MC/9 cells is conducted. To that end, an attempt was first made to dissolve the peptides in complete medium at the concentration of 1 mg/mL. Due to the fact that, of the 26 peptides of Table 1, only 10 were soluble and 2 were partially soluble in these conditions (Table 3), it was necessary to improve the solubility of the remaining peptides by adding different proportions of dimethyl sulfoxide (DMSO) or urea. Other solubilizing agents, such as guanidine hydrochloride, ethanol, methanol, isopropanol, dimethylformamide (DMF), acetone, acetonitrile, ammonia and acetic acid were also tested, but due to the fact that they were not very effective or toxic for the cells, their use was discarded. For the purpose of limiting as much as possible the toxicity of DMSO or urea, the concentration of both agents in the culture medium was kept as low as possible compatible with the in vitro assay. Thus, the maximum concentration of solubilizing agent to be added which allows conducting the in vitro proliferation assay of MC/9 cells was first determined. As indicated above, 1, 0.5, 0.1, 0.05, 0.01, 0.005 and 0.001% acetic acid, ammonia, DMSO, DMF, acetone, acetonitrile, isopropanol, methanol and ethanol and 2, 1, 0.5, 0.250, 0.125, 0.062 and 0.031 M urea and guanidine hydrochloride were tested.

Guanidine hydrochloride was very toxic in all tested concentrations. The final maximum concentration, compatible with the assay, of acetic acid, DMSO and DMF was 0.01 or 0.005%, which concentrations do not allow solubilizing the peptides. In the case of urea, the limit concentration was 125 mM, and for ammonia, 0.2% (maximum tested). In relation to the alcohols, they were compatible up to 1% (maximum) and acetone and acetonitrile seemed to induce MC/9 cell proliferation. DMSO:

The resuspension of the peptides identified as SEQ ID NO: 5, SEQ ID NO: 6, SEQ ID NO: 9, SEQ ID NO: 12, SEQ ID NO: 15 and SEQ ID NO: 16 with DMSO (2% of the final volume of the 1 mg/mL stock) and clean medium was tested. After subjecting them to sonication, all of them were still cloudy, except the peptide identified as SEQ ID NO: 16.

Methanol/Ethanol

To dissolve peptides using these alcohols, it is necessary to use them at 100% and at this concentration they are toxic for MC/9 cells. They are toxic even at 70%.

Urea

The peptides identified as SEQ ID NO: 6, SEQ ID NO: 16, SEQ ID NO: 17, SEQ ID NO: 18 and SEQ ID NO: 20 were dissolved in 8 M urea (final concentration 0.8 M in 1 mg/mL) and complete medium. Urea is relatively toxic (cpm without urea 1.128, with 120 mM urea 109, with 80 mM 308 and with 20 mM 800, but the window is maintained).

The conditions used to solubilize the peptides are summarized in Table 3. Of the total of 39 peptides indicated, 11 (in bold print) could not be solubilized with any of the indicated conditions, therefore they could not be tested in the in vitro assay.

TABLE 3

Conditions used to solubilize 1 mg/mL peptides

| SEQ ID NO: | Complete medium | 2% DMSO | 0.8 M UREA |
|---|---|---|---|
| 1 | S | | |
| 2 | S | | |
| 3 | I | | |
| 4 | S | | |
| 5 | I | Turbidity | Turbidity |
| 6 | I | Turbidity | S |
| 7 | S | | |
| 8 | S | | |
| 9 | I | Turbidity | Turbidity |
| 10 | S | | |
| 11 | S | | |
| 12 | I | Turbidity | Turbidity |
| 13 | S | | |
| 14 | S | | |
| 15 | I | Turbidity | Turbidity |
| 16 | I | part S | S |
| 17 | I | | part S |
| 18 | I | | S |
| 19 | S | | |
| 20 | I | | S |
| 21 | I | | Turbidity |
| 22 | part S | | |
| 23 | I | | Turbidity |
| 24 | I | | Turbidity |
| 25 | part S | | |
| 26 | I | | Turbidity |

The peptides which could not be solubilized with any of the tested conditions are indicated in bold print. part S: partially soluble; S: soluble; I: insoluble The addition of peptides with the capacity to inhibit the activity of IL-10 to the MC/9 cell culture, to which exogenous IL-10 has been added, has the effect of inhibiting the proliferation of these cells due to the fact that IL-10 promotes the proliferation thereof. However, the addition of a peptide or any component to the culture (used to improve peptide solubility) which was toxic for MC/9 cells would also have the effect of inhibiting cell proliferation. For this reason, to assure that a peptide really inhibits IL-10, and not the proliferation due to toxicity on the cells, it is necessary to show that the peptide or other agent which is added to the culture is not toxic for the cells. For this purpose, an assay in parallel of the peptides using mouse granulocyte-monocyte colony-stimulating factor (mGM-CSF) (which also promotes MC/9 cell proliferation) instead of IL-10 was conducted. The concentration of mGM-CSF used was 0.01 ng/mL. In this case, IL-4 was not used as co-stimulus. The toxicity was expressed as the percentage of inhibition of the proliferation induced by mGM-CSF.

In the case of the peptides dissolved in urea, when analyzing both the IL-10 inhibition and the toxicity, negative, positive controls and controls with antibody with the concentrations of urea present in the peptide sample (120 mM, 80 mM and 20 mM) as well as controls without urea were included. The percentage of inhibition at each concentration of peptide was calculated comparing the cpm values of the sample with the values of the controls which contained the same concentration of urea.

Figure 4A:
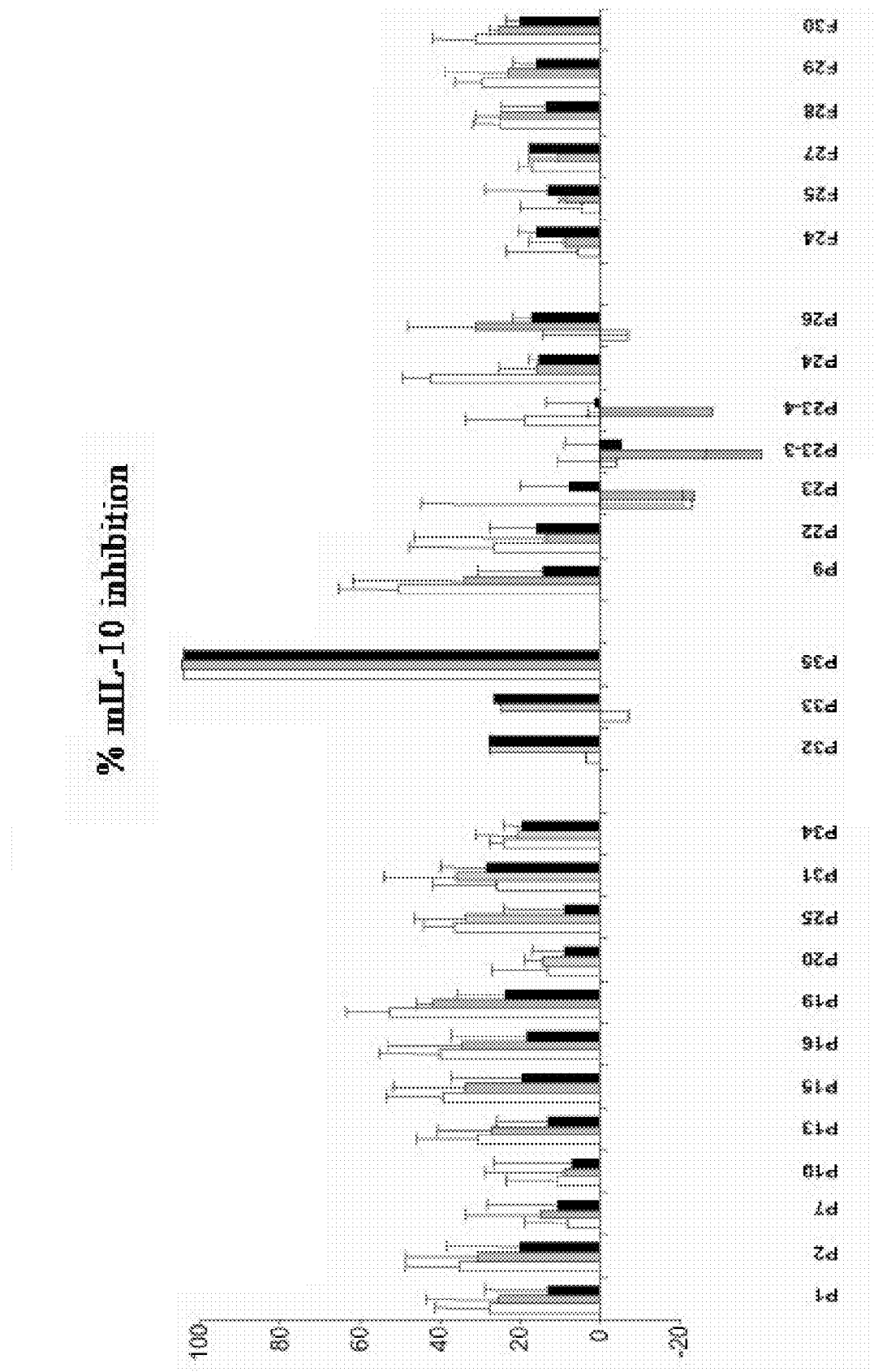
FIG. 4 consists of bar graphs indicating the percentage of inhibition of human IL-10 (hIL-10) and of murine IL-10 (mIL-10) obtained with each peptide at the concentration of 150, 100 and 50 µg/mL (from left to right) (FIG. 4A), and the percentage of toxicity [expressed as the percentage of inhibition of MC/9 cell proliferation by the granulocyte macrophage-colony stimulating factor (GM-CSF) (FIG. 4B). Each bar corresponds to an average of 2 or 3 independent experiments.
Figure 4B:
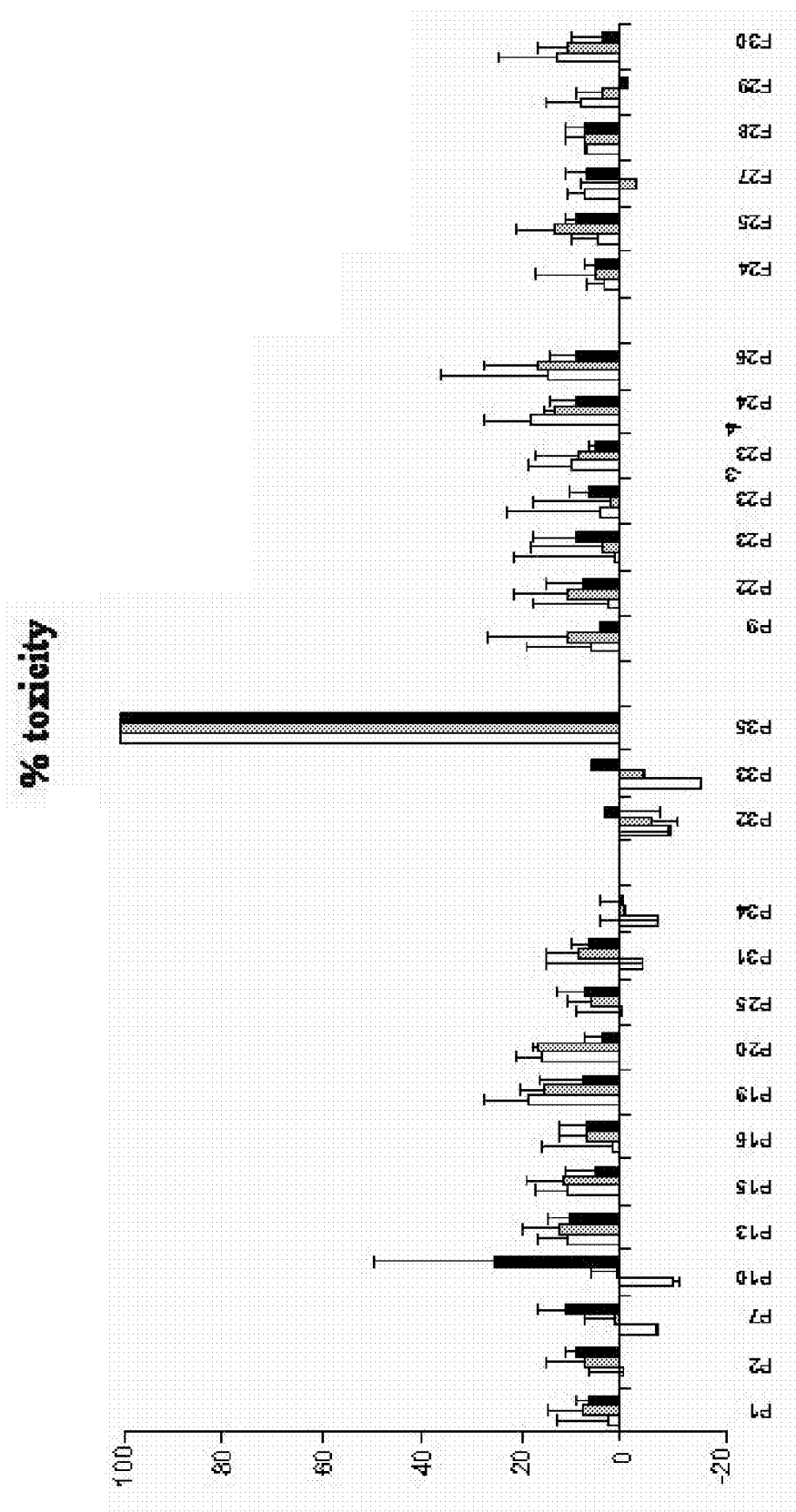

Upon taking into account the percentage of inhibition of IL-10 by the peptides indicated in FIG. 4 [P1 (SEQ ID NO: 1), P2 (SEQ ID NO: 2), P7 (SEQ ID NO: 4), P9 (SEQ ID NO: 6), P10 (SEQ ID NO: 7), P13 (SEQ ID NO: 8), P15 (SEQ ID NO: 10), P16 (SEQ ID NO: 11), P19 (SEQ ID NO: 13), P20 (SEQ ID NO: 14), P22 (SEQ ID NO: 16), P23 (SEQ ID NO: 17), P23-3 (SEQ ID NO: 43), P23-4 (SEQ ID NO: 44), P24 (SEQ ID NO: 18), P25 (SEQ ID NO: 19), P26 (SEQ ID NO: 20), P31 (SEQ ID NO: 22), P32 (SEQ ID NO: 23), P33 (SEQ ID NO: 24), P34 (SEQ ID NO: 25), P35 (SEQ ID NO: 26), F24 (SEQ ID NO: 30), F25 (SEQ ID NO: 31), F27 (SEQ ID NO: 33), F28 (SEQ ID NO: 34), F29 (SEQ ID NO: 35) and F30 (SEQ ID NO: 36)], together with their toxicity, it is observed that:

of the 12 peptides of Table 3 which were soluble or partially soluble in complete medium, the peptides identified as P7 (SEQ ID NO: 4), P10 (SEQ ID NO: 7) and P20 (SEQ ID NO: 14) (FIG. 4) did not have significant inhibitory activity for hIL- or mIL-10 (values around 10%-20% of inhibition); the remaining peptides had IL-10 inhibitory activities comprised between 30% and 50%, the peptides identified as P15 (SEQ ID NO: 10), P19 (SEQ ID NO: 13), P25 (SEQ ID NO: 19) and P34 (SEQ ID NO: 25) being the most active;

in relation to the peptides which were dissolved using urea [the peptides identified as P9 (SEQ ID NO: 6), P22 (SEQ ID NO: 16), P23 (SEQ ID NO: 17), P23-3 (SEQ ID NO: 43), P23-4 (SEQ ID NO: 44), P24 (SEQ ID NO: 18) and P26 (SEQ ID NO: 20)], the peptides identified as P9 (SEQ ID NO: 6) and P22 (SEQ ID NO: 16) were very active, with IL-10 inhibitory activities around 60%; the remaining peptides of this group were not active, and the peptides identified as P24 (SEQ ID NO: 18) and P26 (SEQ ID NO: 20) were partially toxic for MC/9 cells; and in the group of the predicted peptides based on considerations of "complementarity" with IL-10 sequence regions (Example 2) [the peptides identified as F24 (SEQ ID NO: 30), F25 (SEQ ID NO: 31), F27 (SEQ ID NO: 33), F28 (SEQ ID NO: 34), F29 (SEQ ID NO: 35) and F30 (SEQ ID NO: 36)], the peptides identified as F28 (SEQ ID NO: 34), F29 (SEQ ID NO: 35) and F30 (SEQ ID NO: 36) also show some IL-10 inhibitory activity.

Example 4

In Vitro Inhibition of the Biological Activity of Karpas Regulatory T Cells by Means of Peptides with the Capacity to Bind to IL-10 in Assays for Inhibiting Mixed Lymphocyte Response (MLR)

Figure 5:
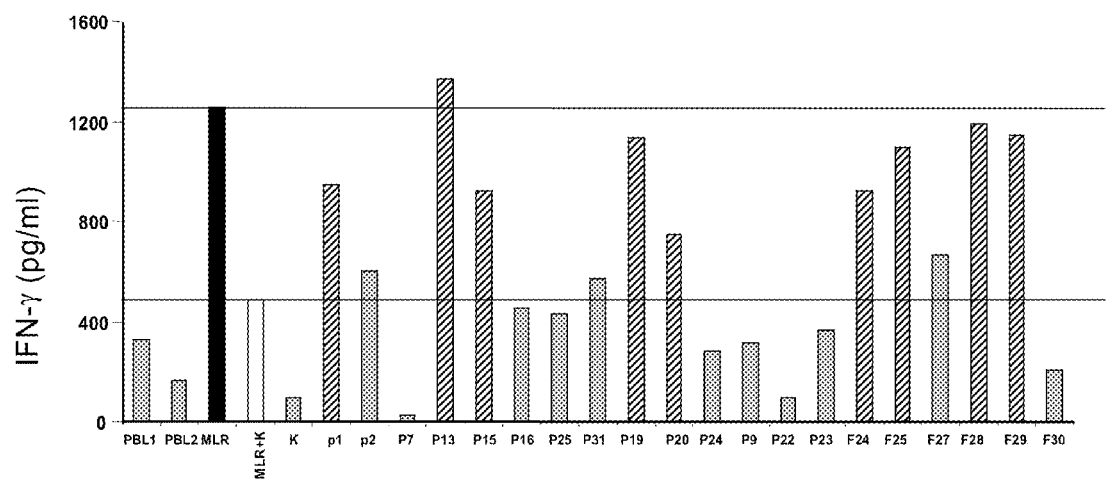
FIG. 5 is a bar graph showing the effect of several peptides with the capacity to bind to IL-10 on the immunosuppressive activity of the Karpas (IL-10 producers) cell line. A "mixed lymphocyte reaction" (MLR) assay was conducted with these cells in which the IFN-γ levels produced were measured as an immune response measurement. The peptides with significant IL-10 inhibitory capacity and which can restore the IFN-γ levels of the MLR are indicated with striped bars. Legends: PBL: peripheral blood lymphocytes, PBL1 and PBL2: peripheral blood lymphocytes from two different healthy donors (by definition, the mixture of these cells induces a proliferative activation by allogeneic recognition through the reaction between MHC and TLR), MLR: mixed lymphocyte reaction, MLR+K: mixed lymphocyte reaction+ Karpas 299 cell line, K: Karpas 299 cell line).

The existence of the Karpas 299 cell line (DSMZ ACC 31), derived from a human lymphoma, with an IL-10-producing and regulatory T cell profile, has been recently described in the literature. With these cells, a "mixed lymphocyte reaction" or MLR was conducted. This technique is based on IFN-γ production in the co-culture of lymphocytes of different origin, with different histocompatibilities, which will recognize each other as foreign. This reaction makes lymphocytes proliferate secreting cytokines, including IFN-γ. For this assay, 100,000 cells of each donor (MLR positive control) alone or with increasing amounts of Karpas 299 cells (0-100,000 Karpas 299) were cultured in 96-well plates. For measuring the activity of the peptides, 100 μg/mL of each peptide per well were added. After 48 hours, aliquots of the supernatants were removed to measure IFN-γ. In this case, it was not possible to measure cell proliferation due to the fact that the existence of the Karpas 299 cell line masks any possible effect in MLR proliferation. The results of the IFN-γ measurement are shown in FIG. 5.

In this assay, peptides P1 (SEQ ID NO: 1), P13 (SEQ ID NO: 8), P15 (SEQ ID NO: 10), P19 (SEQ ID NO: 13), P20 (SEQ ID NO: 14), F24 (SEQ ID NO: 30), F25 (SEQ ID NO: 31), F28 (SEQ ID NO: 34) and F29 (SEQ ID NO: 35) stood out as IL-10 activity inhibitors.

Example 5

Effect of Peptides with the Capacity to Bind to IL-10 [P9 (SEQ ID NO: 6) and P13 (SEQ ID NO: 8)] on the Induction of In Vitro Th1 Response after Immunization with Th0 Determinants, by Means of Quantifying Interferon-Gamma (IFN-γ) Produced in Supernatants After In Vitro Lymphocyte Re-Stimulation The induction of responses of the immune system by means of peptides (antigens) generates specific cytokine profiles depending on the characteristics of the sequence. Helper determinant peptides induce Th0 responses derived from a Th1 profile (cytotoxic response) or Th2 (humoral response), each characterized by its specific cytokine profile. An optimal Th2 profile (defined by the presence of IL-4) is favored by the presence of IL-10 which inhibits the Th1 profile and leads the immune response to a Th2 profile. In this context, treatment with IL-10 inhibitors during the induction of Th0 type response would have a Th1 profile cytokine inducer effect (IFN-γ).

For this study, 6 optimized peptides, 3 derived from ovalbumin (OVA) and 3 derived from myoglobin (MIO) of sperm whale (FISEA) (Table 4) have been chosen as Th0 determinants.

TABLE 4

| Th0 determinant peptides derived from OVA and FISEA | | | |
|---|---|---|---|
| Peptide | Characteristics | Sequence | SEQ ID NO: |
| FISEA | MIO (106-118), not modified | FISEAIIHVLHSR | 37 |
| FISEA G | MIO (106-118; 108G) | FIGEAIIHVLHSR | 38 |
| FISEA K | MIO (106-118; 113K)* | FISEAIIKVLHSR | 39 |
| OVA F | OVA (323-337; 323 F) | ESQAVHAAHAEINEA | 40 |
| OVA G | OVA (323-337; 323 G) | GSQAVHAAHAEINEA | 41 |
| OVA K | OVA (323-337; 323 K)* | KSQAVHAAHAEINEA | 42 |

IL-10-inhibiting peptides used to conduct this assay were peptides P9 (SEQ ID NO: 6), insoluble, and P13 (SEQ ID NO: 8), soluble. Briefly, 4 to 6 week-old female BALB/c mice were subcutaneously immunized with 200 μL of a 1:1 emulsion of Freund's incomplete adjuvant and an aqueous solution containing 50 nmoles of the corresponding Th0 determinant peptide. After 10 days of immunization, the animals were sacrificed and the inguinal, periaortic and popliteal lymph nodes, as well as the spleens were extracted. The extracted lymphocytes were cultured for 48 hours in a 96-well U-bottom plate, in the presence or absence of the peptide used in the immunization at a concentration of 30 mg/ml, and in the presence or absence of IL-10-inhibiting peptides [P9 (50 mg/ml) and P13 (100 mg/ml)] in a final volume of 200 μl of complete medium (MC; RPMI 1640, 10% FBS; 2 mM glutamine, 100 U/ml penicillin; 100 μg/mL streptomycin; $5 \times 10^5$ M 2 β-mercaptoethanol; 25 mM Hepes and 0.5% (v/v) sodium pyruvate). After 48 hours of culture at 37° C. and with 5% CO$_2$, 100 μL of supernatant per well (50 μL for quantifying IFN-γ+50 μL for quantifying IL-10) were taken. The supernatants were frozen at a temperature of −20° C. until determining the cytokines by means of the ELISA technique.

Figure 6:
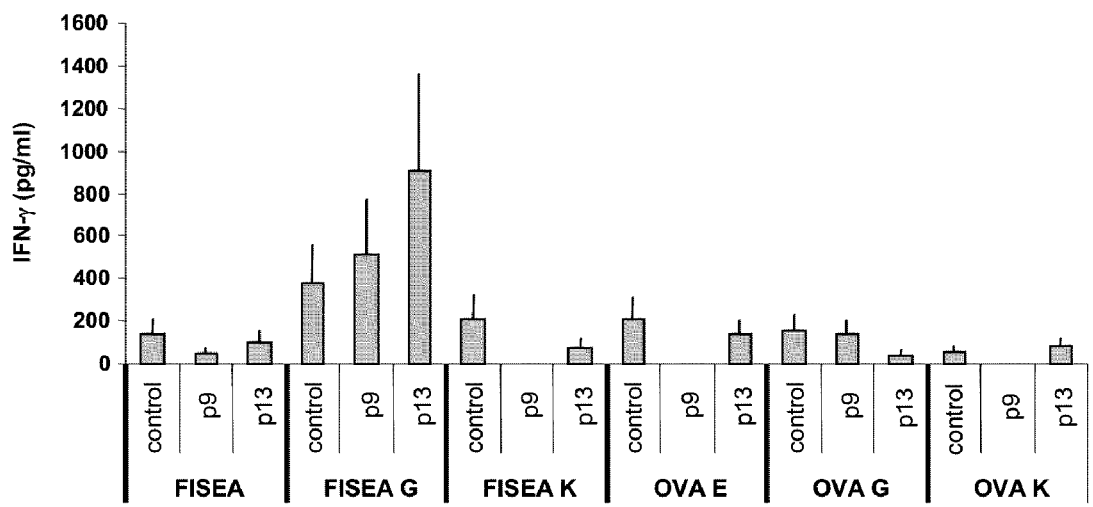
FIG. 6 is a bar graph showing the in vitro effect of peptides P9 (SEQ ID NO: 6) and P13 (SEQ ID NO: 8) in the restimulation of lymphocytes with different T helper determinant peptides (Th0), quantified as IFN-γ production. The inhibition of IL-10 in this system would favor a Th1 cytokine profile and, therefore, an increase of IFN-γ. Peptide FISEA G (SEQ ID NO: 38) was the only peptide that induced detectable IL-10 levels in supernatants together with the highest IFN-γ levels. Peptides P9 (SEQ ID NO: 6) and P13 (SEQ ID NO: 8) increase IFN-γ production only in this case.

In this assay, it has been found that the lymphocytes from the animals immunized with peptide FISEA G (SEQ ID NO: 38), after being re-stimulated in vitro with this peptide, produced the highest IFN-γ levels with respect to the remaining peptides tested (FIG. 6). Furthermore, these IFN-γ levels clearly increased in the presence of peptides P9 (SEQ ID NO: 6) and P13 (SEQ ID NO: 8) by a mechanism compatible with the inhibition of IL-10 (FIG. 6). In fact, this peptide [FISEA G (SEQ ID NO: 38)] has been the only one that has induced detectable IL-10 levels (70 μg/mL) in the supernatants.

Example 6

Effect of Peptides with the Capacity to Bind to IL-10 [P9 (SEQ ID NO: 6) and P13 (SEQ ID NO: 8)] on the Induction of Antitumor Response After the Subcutaneous Inoculation of CT26 Cells IL-10 is a cytokine with a potent immunosuppressive effect related to tumor growth. It is therefore a cytokine generated by many tumors as mechanism to prevent an effective immunologic response.

In this example, the effect of peptides P9 (SEQ ID NO: 6) and P13 (SEQ ID NO: 8) was tested in a tumor growth model after the subcutaneous inoculation of CT26 cells [a mouse colon adenocarcinoma cell line (Fearon, E. R., Vogelstein, B. 1990. A genetic model for colorectal tumorigenesis. Cell 61:759)], in the presence or absence of intratumoral immunotherapy with adjuvants: polyinosinic-polycytidylic acid (poly I:C) and an anti-CD40 agonist antibody for the activation of dendritic, NK and T cells, and subsequent induction of an antitumor cytotoxic response.

In this assay, Balb/C mice were challenged with 5×10$^5$ CT26 tumor cells subcutaneously inoculated with 200 μL of PBS, divided into 4 groups:

(1) Control group: mice inoculated with CT26 cells.

(2) Adjuvant Group: mice treated with 50 μg of poly I:C and 50 μg anti-CD40 by an intratumoral route in 100 μL of PBS on days 0, 7 and 14.

(3) Inhibitor group: mice treated only with IL-10 inhibitors, 50 μg of P9 (SEQ ID NO: 6) by an intratumoral route and 50 μg of P13 (SEQ ID NO: 8) by an intraperitoneal route per mouse, three times per week in PBS, for 3 weeks.

(4) Complete Group: mice treated with adjuvants plus IL-10 inhibitors.

Day "0" was considered when the tumor had reached a diameter of 5-6 mm.

Figure 7:
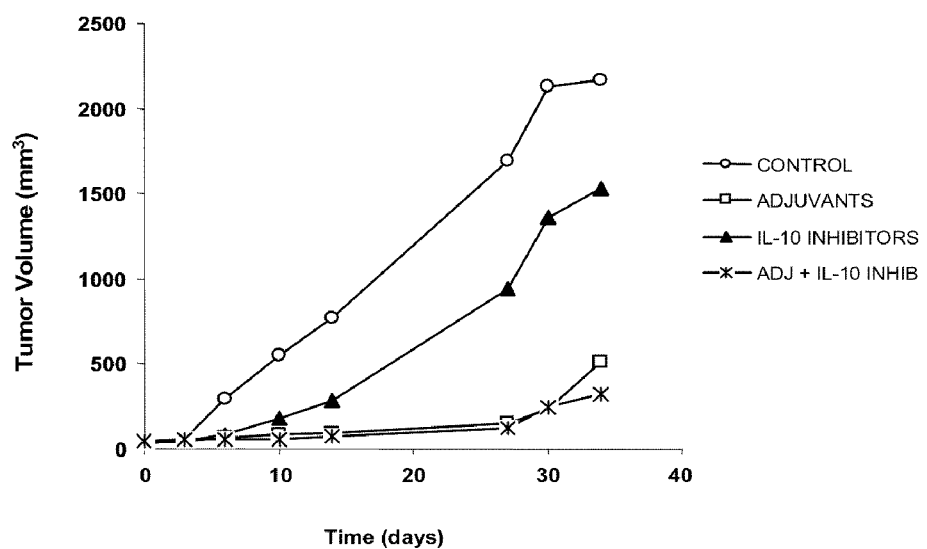
FIG. 7 is a diagram showing the average tumor growth in different groups of BALB/c mice subcutaneously inoculated with $5 \times 10^5$ tumor cells (CT26). The different groups show the average tumor growth in the absence of treatments (Control group), treated with poly I:C and anti-CD-40 antibody (Adjuvants), treated with peptides P9 (SEQ ID NO: 6) (intratumorally) and P13 (SEQ ID NO: 8) (intraperitoneally) (IL-10 inhibitors) or a combination of adjuvants and IL-10 inhibitors (Adj+IL-10 Inhib).

The treatment with IL-10-inhibiting peptides was capable of protecting 6.6% of the animals and generating a considerable delay in tumor growth (FIG. 7). The adjuvants protected 53% of the animals and drastically decreased the tumor growth average (FIG. 7). The combination of adjuvants and IL-10 inhibitors slightly delayed the tumor growth average with respect to the group treated with adjuvants alone (FIG. 7), but increased the percentage of protection against the tumor up to 76.6%.

This example clearly shows the applicability of IL-10-inhibiting peptides in the context of the immunosuppression mediated by this factor in tumor development.

Example 7

Biomolecular Interaction Between Human IL-10 and Peptides with the Capacity to Bind to IL-10 [P9 (SEQ ID NO: 6) and P13 (SEQ ID NO: 8)] and Derivatives thereof Determined by Means of Surface Plasmon Resonance Analysis By means of a surface plasmon resonance (SPR) analysis, the biomolecular interaction between human IL-10 and peptides P9 (SEQ ID NO: 6) and P13 (SEQ ID NO: 8), as well as of the following truncated and/or modified forms of P9 was measured:

TABLE 5

| Peptide | Sequence*) | SEQ ID NO: |
|---|---|---|
| P9 (2-15) | HRCFHFRRHPVAVF | 45 |
| P9 (1-14) | CHRCFHFRRHPVAV | 46 |
| P9 (1-13) | CHRCFHFRRHPVA | 47 |
| P9 (2-14) | HRCFHFRRHPVAV | 48 |
| P9 (2-13) | HRCFHFRRHPVA | 49 |
| P9 (3-14) | RCFHFRRHPVAV | 50 |
| P9 (15 Ala) | CHRCFHFRRHPVAVA | 51 |
| P9 (14 Ala) | CHRCFHFRRHPVAF | 52 |
| P9 (1-13; 1 Ser) | SHRCFHFRRHPVA | 53 |

*) amino acid nomenclature in one-letter code

As can be seen in Table 5:

SEQ ID NO: 45 [P9(2-15)] is a peptide comprising the sequence of amino acids 2-15 of peptide P9 (SEQ ID NO: 6);

SEQ ID NO: 46 [P9(1-14)] is a peptide comprising the sequence of amino acids 1-14 of peptide P9 (SEQ ID NO: 6);

SEQ ID NO: 47 [P9(1-13)] is a peptide comprising the sequence of amino acids 1-13 of peptide P9 (SEQ ID NO: 6);

SEQ ID NO: 48 [P9(2-14)] is a peptide comprising the sequence of amino acids 2-14 of peptide P9 (SEQ ID NO: 6);

SEQ ID NO: 49 [P9(2-13)] is a peptide comprising the sequence of amino acids 2-13 of peptide P9 (SEQ ID NO: 6);

SEQ ID NO: 50 [P9(3-14)] is a peptide comprising the sequence of amino acids 3-14 of peptide P9 (SEQ ID NO: 6);

SEQ ID NO: 51 [P9(15 Ala)] is a peptide comprising the amino acid sequence of peptide P9 (SEQ ID NO: 6) in which the amino acid present in position 15 (Phe) has been replaced by Ala;

SEQ ID NO: 52 [P9(14 Ala)] is a peptide comprising the amino acid sequence of peptide P9 (SEQ ID NO: 6) in which the amino acid present in position 14 (Val) has been replaced by Ala; and SEQ ID NO: 53 [(1-13; 1 Ser)] is a peptide comprising the sequence of amino acids 1-13 of peptide P9 (SEQ ID NO: 6) and in which the amino acid present in position 1 (Cys) has been replaced by Ser.

To perform this assay, the Biosensor BIAcore X (BIAcore, AB, Uppsala, Sweden) was used. Briefly, human recombinant protein IL-10 (R & D Systems, cat No. 217-IL/CF) was covalently immobilized on the surface of flow cell 2 (FC2) of a CM5 chip (BIAcore), as described in De Crescenzo et al. 2001 (JBC, Vol 276; 29632-29643). Flow cell 1 (FC1), on the surface of which IL-10 is not immobilized, was used as a reference flow cell. The peptide solutions (10 μM) were injected at least twice in 10 mM Hepes buffer, pH 7.4, 150 mM NaCl, 0.005% Tween 20 (Polyoxyethylene Sorbitan Monolaurate) at a flow of 30 µl/min. The binding curves were processed by means of subtracting the response in FC1 from that obtained in FC2. The response in equilibrium was compared between the test peptide and an irrelevant control peptide of the same length. The control peptide used was peptide P301 (SEQ ID NO: 54) (derived from the HIV-1 coat, gp120 (301-315): NNTRKRIRIQRGPGR). Each response was multiplied by a mass correction factor: MW(PX)/MW(P), where MW(PX) is the molecular weight of the test peptide P and MW(P) is the molecular weight of the control peptide (P301). It was observed that the different peptides tested gave a positive signal, which clearly shows their capacity to bind specifically to IL-10.

Figure 8:
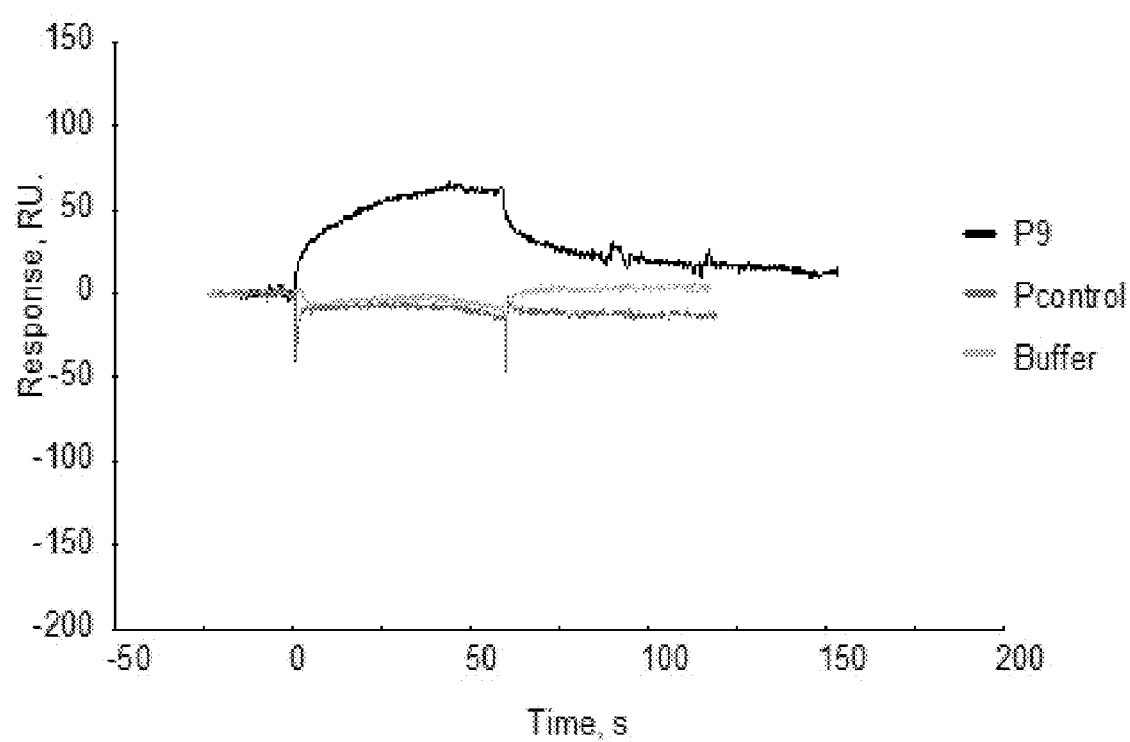
FIG. 8 is a graph showing the biomolecular interaction profile, obtained by means of a surface plasmon resonance (SPR) analysis, which occurs between IL-10 and peptide P9 (SEQ ID NO: 6), as well as that obtained with the control peptide [P301 (SEQ ID NO: 54)].

FIG. 8 shows an example of the biomolecular interaction profile, obtained by means of a SPR analysis, which occurs between IL-10 and peptide P9 (SEQ ID NO: 6), as well as that obtained with the control peptide [P301 (SEQ ID NO: 54)].

Figure 9:
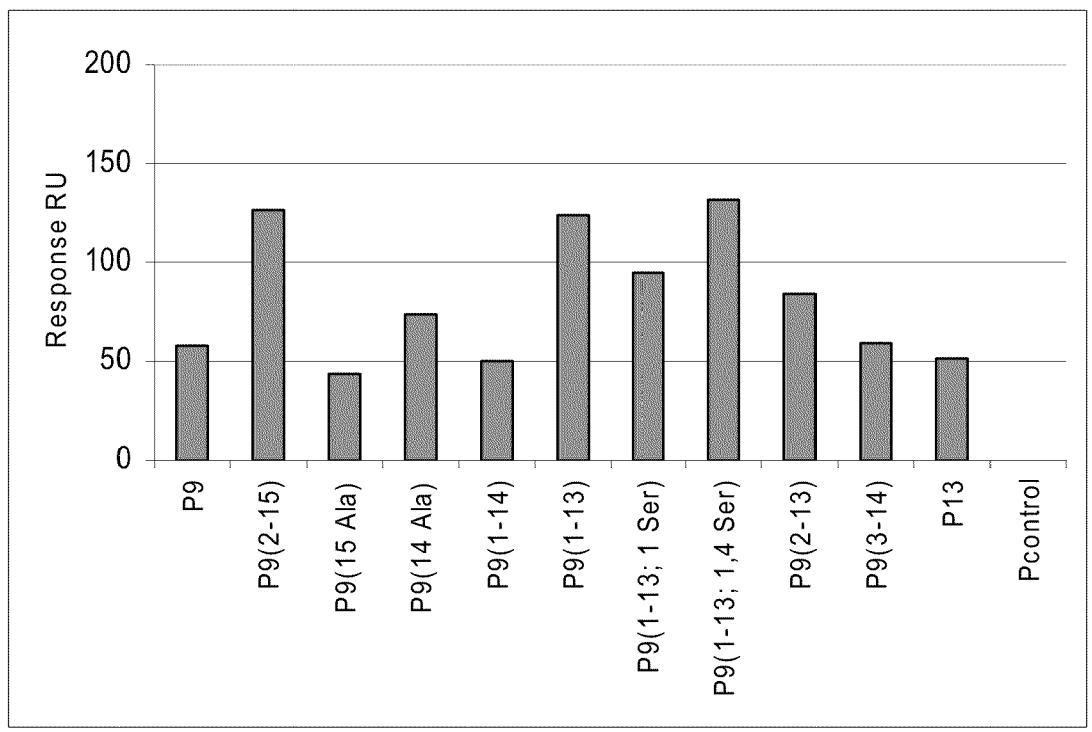
FIG. 9 is a bar graph showing the results obtained from the biomolecular interaction, measured by means of SPR analysis, which occurs between IL-10 and peptides P9 (SEQ ID NO: 6), P13 (SEQ ID NO: 8) and their truncated and/or modified forms: P9(2-15) (SEQ ID NO: 45), P9(1-14) (SEQ ID NO: 46), P9(1-13) (SEQ ID NO: 47), P9(2-14) (SEQ ID NO: 48), P9(2-13) (SEQ ID NO: 49), P9(3-14) (SEQ ID NO: 50), P9(15 Ala) (SEQ ID NO: 51), P9(14 Ala) (SEQ ID NO: 52), P9(1-13; 1 Ser) (SEQ ID NO: 53).

FIG. 9 shows the results obtained from the biomolecular interaction, measured by means of SPR analysis, which occurs between IL-10 and peptides P9 (SEQ ID NO: 6), P13 (SEQ ID NO: 8) and their truncated and/or modified forms: P9(2-15) (SEQ ID NO: 45), P9(1-14) (SEQ ID NO: 46), P9(1-13) (SEQ ID NO: 47), P9(2-14) (SEQ ID NO: 48), P9(2-13) (SEQ ID NO: 49), P9(3-14) (SEQ ID NO: 50), P9(15 Ala) (SEQ ID NO: 51), P9(14 Ala) (SEQ ID NO: 52), P9(1-13; 1 Ser) (SEQ ID NO: 53).

In general, a good interaction was found between IL-10 and the assayed peptides. When analyzing peptides derived from P9 (SEQ ID NO: 6), it was observed that the modification of an amino acid at the carboxyl terminal end did not affect their capacity to bind to IL-10; however, in the case of peptides truncated at their amino or carboxyl terminal end, an improvement in the capacity of the peptide to bind to IL-10 was found.

Example 8

Inhibitory Effect of Peptides P9 (SEQ ID NO: 6) and P13 (SEQ ID NO: 8) with the Capacity to Bind to IL-10 on the Phosphorylation of Transcription Factor STAT3 Induced by the Binding of IL-10 to its Membrane Receptor The activity of IL-10 is mediated by the binding to a specific membrane receptor, IL-10R, which is expressed in a wide variety of immune cells. The IL-10/IL-10R interaction attracts and captures 2 kinases (Jak1 and Tyk2) phosphorylating and activating the transcription factor STAT3 (Signal Transducer and Activator of Transcription 3), which is found in inactive form in the cytoplasm and is essential for all the known functions of IL-10 (Donnelly et al., Journal of Interferon & Cytokine Research. Jun. 1, 1999, 19(6): 563-573).

The capacity of peptides P9 (SEQ ID NO: 6) and P13 (SEQ ID NO: 8) with the capacity to bind to IL-10 to inhibit STAT3 phosphorylation induced by IL-10 was tested. The assay was conducted using MC/9 cells (CRL-8306, American Type Cell Culture (ATCC), Virginia, United States) responding to both human and murine IL-10. In a 96-well U-bottom plate (TPP, 92097) and before coming into contact with the cells, peptides P9 (SEQ ID NO: 6) and P13 (SEQ ID NO: 8) were incubated at a concentration of 50 µg/ml, with a concentration of 0.15 ng/ml of IL-10 for two hours at 37° C. and 5% $CO_2$ in a volume of 100 µl of complete medium (RPMI 1640, 10% fetal bovine serum (FBS); 2 mM glutamine, 100 U/ml penicillin; 100 µg/mL streptomycin; $5 \times 10^5$ M β-mercaptoethanol; 25 mM Hepes and 0.5% (v/v) sodium pyruvate). Then, $2 \times 10^5$ cells/well were added and incubated for another two hours at 37° C. and 5% $CO_2$ in a final volume of 200 µl/well. After centrifuging the cells at 1,500 rpm for 5 minutes and discarding the supernatant, the pellet was resuspended in 150 ml of loading buffer for electrophoresis (10% glycerol, 5% 2-mercaptoethanol, 2% sodium dodecyl sulphate, Tris-HCl 62.5 mM [pH 6.8], 0.006% bromophenol blue) and the samples were frozen at −80° C. From these samples, a Western Blot was performed to determine the amount of phosphorylated STAT-3 in the different conditions assayed, including a negative control (only cells) and a positive control (cells+ IL-10). The amount of actin in each sample was also determined as an analysis control. The bands obtained in the Western Blot were analyzed in a densitometer to quantify the content of each of them. The densitometer readings obtained for each sample were corrected with the corresponding actin control.

Figure 10:
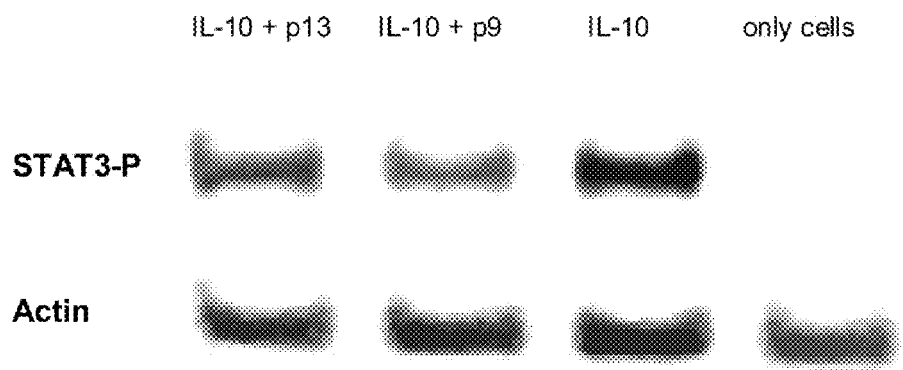
FIG. 10 shows the inhibitory effect of peptides P9 (SEQ ID NO: 6) and P13 (SEQ ID NO: 8) on STAT3 phosphorylation induced by IL-10. The phosphorylated-STAT3 expression was analyzed by means of the Western Blot technique (FIG. 10A). The bar graph (FIG. 10B) shows the ratio between the content of the phosphorylated-STAT3 bands, quantified by means of densitometry, and that obtained in the actin control for each sample.
Figure 10:
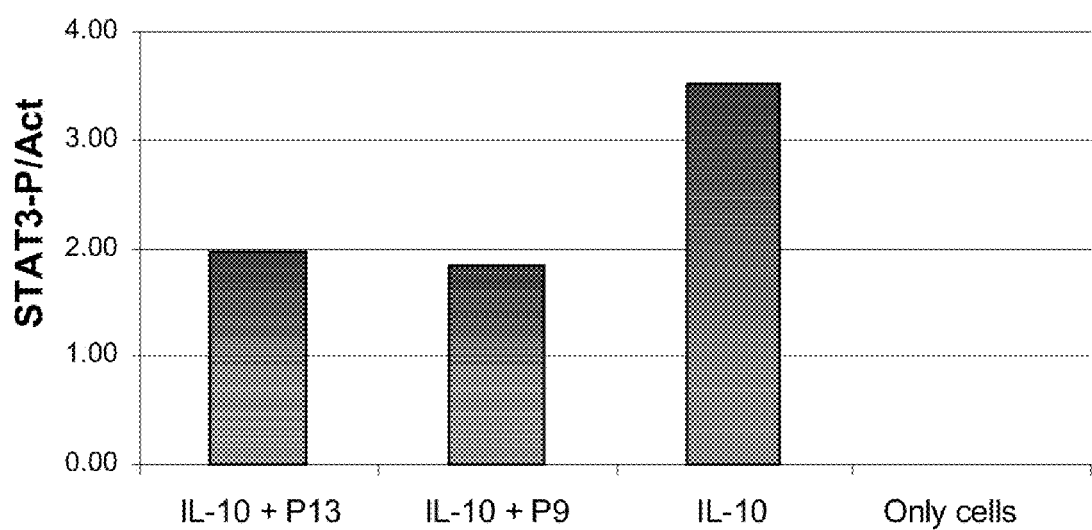

FIG. 10 shows the inhibitory effect of peptides P9 (SEQ ID NO: 6) and P13 (SEQ ID NO: 8) on STAT3 phosphorylation induced by IL-10. The phosphorylated-STAT3 expression was analyzed by means of Western Blot (FIG. 10A). FIG. 10B shows the ratio between the content of the phosphorylated-STAT3 bands, quantified by means of densitometry, and that obtained in the actin control for each sample.

Example 9

Effect of IL-10-Inhibiting Peptides in Proliferation Assays with B16-F10 Tumor Cells The IL-10 immunosuppressive effect has been related to tumor growth, such IL-10 being a cytokine generated by many tumors for evading an effective immunological response. In fact, certain tumor cells constitutively secrete IL-10, which is essential for malignant cell proliferation, it having been demonstrated that their neutralization decreases their growth. This is the case of the B16-F10 (B16) murine melanoma tumor line, which secretes considerable amounts of IL-10 and the proliferation of which is inhibited in the presence of an IL-10-neutralizing antibody.

Figure 11:
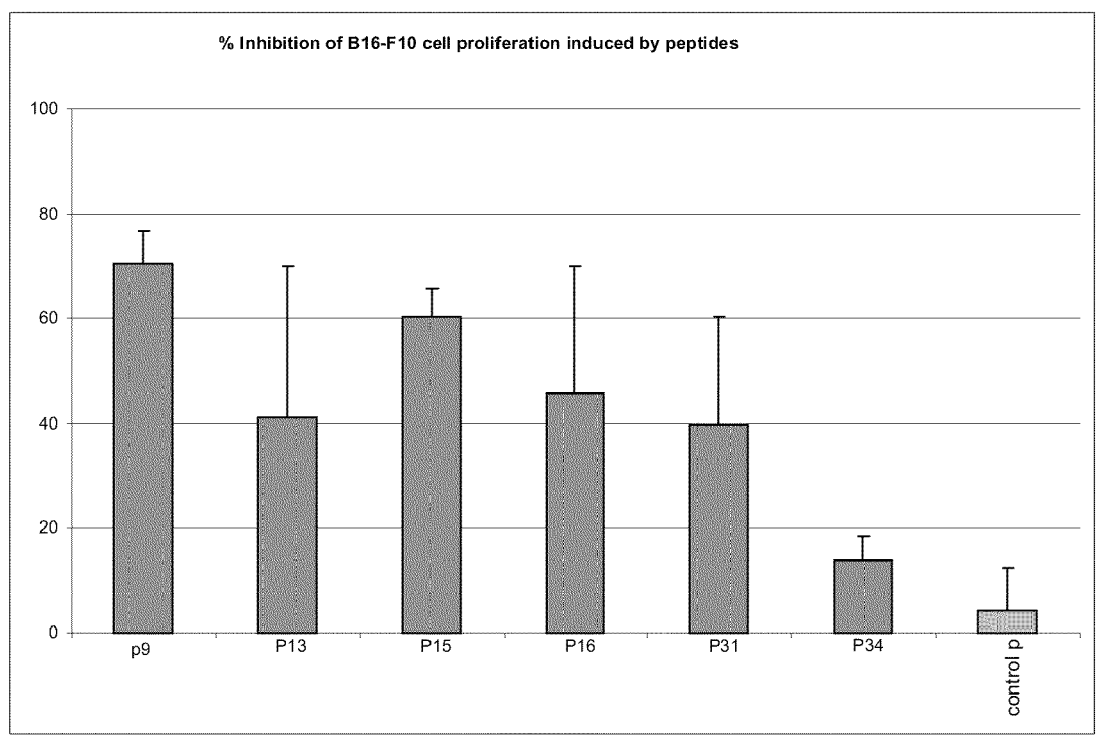
FIG. 11 shows in a bar graph the percentage of inhibition of cell proliferation induced by peptides P9 (SEQ ID NO: 6), P13 (SEQ ID NO: 8), P15 (SEQ ID NO: 10), P16 (SEQ ID NO: 11), P31 (SEQ ID NO: 22) and P34 (SEQ ID NO: 25), as well as that induced by control peptide P301 (SEQ ID NO.

In this assay, the activity of IL-10-inhibiting peptides on the proliferation of B16 cells requiring this cytokine for their growth was tested. To conduct the assay, 5,000 cells per well in RPMI medium supplemented with 2% FBS were cultured in a 96-well plate (Tissue Culture Plate, 96 W, Flat Bottom, with Lid, Sterile, CELLSTAR N° 655180), in the presence or absence of peptides: P9 (SEQ ID NO: 6), P13 (SEQ ID NO: 8), P15 (SEQ ID NO: 10), P16 (SEQ ID NO: 11), P31 (SEQ ID NO: 22) and P34 (SEQ ID NO: 25); peptide P301 (SEQ ID NO: 54) was used as a negative control. The assayed concentration of peptide was 200 µg/ml. The cells were thus incubated for 24 hours at 37° C. and 5% $CO_2$. After this time had elapsed, the cells were stained with crystal violet and the dye was quantified by means of washing with 10% acetic acid and measured in the ELISA reader at 570 nm. All peptides were tested at a concentration of 200 µg/ml. The obtained results are included in FIG. 11 and correspond to the mean and deviations of the assays conducted in triplicate.

Example 10

Effect of Peptide P13 (SEQ ID NO: 8) on the Inhibitory Activity of the Hepatitis C Virus Nucleocapsid (HCV Core) Protein on IFN-α Production in a Peripheral Blood Mononuclear Cell Culture IFN-α production by plasmacytoid dendritic cells (pDCs) is critical in antiviral immune response. In the case of hepatitis C virus (HCV), which has a high chronicity tendency, one of the mechanisms for escaping this response could be mediated by the activation of monocytes after their binding with the HCV core protein through receptor TLR2 (Toll-Like Receptor 2), which stimulates the production of cytokines such as IL-10, which in turn inhibit IFN-α production by pDCs (Dolganiuc et al., The Journal of Immunology, 2006, 177:6758-6768). The stimulation of peripheral blood mononuclear cells (PBMC) with a TLR9 ligand induces the IFN-α production by pDCs and the presence of HCV core inhibits the IFN-α production. This inhibition is at least partly mediated by IL-10 production by monocytes, it was therefore decided to test the effect of peptides with the capacity to bind to IL-10 provided by this invention in this system. To that end, blood samples were obtained from different healthy donors, from which PBMCs were isolated by means of a Ficoll gradient (GE Healthcare, 17-1440-03). In a 96-well U-bottom plate (TPP, 92097) and adding $2 \times 10^5$ cells per well, cells were incubated in RPMI medium supplemented with 10% FBS together with the TLR9 ligand CpG (Genosys, ODN2216) at a concentration of 5 µg/ml, recombinant HCV core (BioDesign, R8A115) at a concentration of 2.5 µg/ml and peptide P13 (SEQ ID NO: 8). Anti-IL-10 antibody (eBioscience, 16-7108-81) at a concentration of 1 µg/ml was used as a positive control. The cells were incubated for 48 hours at 37° C. and 5% $CO_2$. After this time had elapsed, supernatants were taken from each well and IFN-α production was measured by means of the ELISA technique, using a commercial kit (MabTech, 3424-1H-6).

FIG. 12 shows in a bar graph the effect of peptide P13 (SEQ ID NO: 8) on IFN-α production in a PBMC culture stimulated with CpG and in the presence of HCV core, as described previously. The shown results are representative of four experiments with similar results.

The invention claimed is:

1. A peptide comprising 12, 13, 14, or 15 consecutive amino acids of SEQ ID NO: 6, or a pharmaceutically acceptable salt thereof, wherein said peptide has the capacity to bind to IL-10.

2. A peptide according to claim 1, selected from the group consisting of SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52 and SEQ ID NO: 53, and their pharmaceutically acceptable salts.

3. A peptide according to claim 1, wherein said peptide is SEQ ID NO: 6, or a pharmaceutically acceptable salt thereof.

4. An isolated nucleic acid sequence encoding a peptide according to claim 1.

5. A vector comprising a nucleic acid sequence according to claim 4.

6. A pharmaceutical composition comprising a pharmaceutically acceptable carrier and a vector according to claim 5.

7. A host cell comprising a nucleic acid sequence according to claim 4.

8. A process for producing a peptide which comprises growing a host cell according to claim 7 under conditions allowing the production of said peptide and, if desired, the recovery of said peptide.

9. A pharmaceutical composition comprising a pharmaceutically acceptable carrier and a host cell according to claim 7.

10. A pharmaceutical composition comprising a pharmaceutically acceptable carrier and a nucleic acid sequence according to claim 4.

11. A pharmaceutical composition comprising a peptide according to claim 1 together with at least one pharmaceutically acceptable excipient.

12. A pharmaceutical composition according to claim 11, further comprising one or more different IL-10 inhibitor compounds selected from the group consisting of IFN-γ, ammonium trichloro(dioxoethylene-O,O') tellurate, 15-deoxy-delta-12,14-prostaglandin J2, and chimeric murine anti-human CD20 antibody.

13. A peptide selected from the group consisting of SEQ ID NO: 6, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52 and SEQ ID NO: 53, and their pharmaceutically acceptable salts.

* * * * *

UNITED STATES PATENT AND TRADEMARK OFFICE
CERTIFICATE OF CORRECTION

PATENT NO. : 8,148,334 B2  
APPLICATION NO. : 12/593321  
DATED : April 3, 2012  
INVENTOR(S) : Lorea Manterola Careaga et al.

Page 1 of 1

It is certified that error appears in the above-identified patent and that said Letters Patent is hereby corrected as shown below:

Cover Page, Inventor 7: change "Jesús Prieto Valtueñ" to --Jesús Prieto Valtueña--

Signed and Sealed this  
Seventeenth Day of July, 2012

David J. Kappos  
*Director of the United States Patent and Trademark Office*